(12) United States Patent
Drakulic et al.

(10) Patent No.: US 10,456,057 B2
(45) Date of Patent: Oct. 29, 2019

(54) SYSTEMS AND METHODS FOR EVALUATION OF ELECTROPHYSIOLOGY SYSTEMS

(71) Applicant: BIOSIG TECHNOLOGIES, INC., Los Angeles, CA (US)

(72) Inventors: Budimir S. Drakulic, Los Angeles, CA (US); Thomas George Foxall, Surrey (CA); Sina Fakhar, Encino, CA (US); Branislav Vlajinic, Los Angeles, CA (US)

(73) Assignee: BIOSIG TECHNOLOGIES, INC., Los Angeles, CA (US)

( * ) Notice: Subject to any disclaimer, the term of this patent is extended or adjusted under 35 U.S.C. 154(b) by 323 days.

(21) Appl. No.: 15/103,278

(22) PCT Filed: Dec. 12, 2014

(86) PCT No.: PCT/US2014/070165
§ 371 (c)(1),
(2) Date: Jun. 9, 2016

(87) PCT Pub. No.: WO2015/089480
PCT Pub. Date: Jun. 18, 2015

(65) Prior Publication Data
US 2016/0317055 A1 Nov. 3, 2016

Related U.S. Application Data

(60) Provisional application No. 61/915,451, filed on Dec. 12, 2013.

(51) Int. Cl.
*A61B 5/04* (2006.01)
*A61B 5/0452* (2006.01)
(Continued)

(52) U.S. Cl.
CPC ............ *A61B 5/0452* (2013.01); *A61B 5/042* (2013.01); *A61B 5/0472* (2013.01); *A61B 5/7278* (2013.01); *G16H 50/50* (2018.01)

(58) Field of Classification Search
USPC .................................................. 600/508–509
See application file for complete search history.

(56) References Cited

U.S. PATENT DOCUMENTS 5,983,127 A 11/1999 Depinto
8,543,195 B1 9/2013 Brockway et al.
(Continued)

OTHER PUBLICATIONS

International Application No. PCT/US2014/070165 International Report on Patentability dated Jun. 23, 2016.
(Continued)

*Primary Examiner* — Nicole F Lavert
(74) *Attorney, Agent, or Firm* — Wilson Sonsini Goodrich & Rosati

(57) ABSTRACT

A signal processing evaluator and methods that compare a digital waveform of a cardiac signal to a first processed signal generated by a test system such as an EP recorder or an EP mapping system and generates a first finding evaluating how well the test system filters non-cardiac signals or simulated body impedance. A simulator and methods that send cardiac signals including non-cardiac signals or simulated body impedance to a test system and to a signal processing evaluator for evaluation of the test system.

18 Claims, 6 Drawing Sheets

(51) Int. Cl.
*A61B 5/042* (2006.01)
*A61B 5/0472* (2006.01)
*A61B 5/00* (2006.01)
*G16H 50/50* (2018.01)

(56) References Cited

U.S. PATENT DOCUMENTS

| | | | |
|---|---|---|---|
| 2003/0135125 A1* | 7/2003 | Lu | A61B 5/0008 600/510 |
| 2008/0183093 A1* | 7/2008 | Duann | A61B 5/04525 600/516 |
| 2008/0200966 A1 | 8/2008 | Blomberg et al. | |
| 2012/0323130 A1 | 12/2012 | Warner et al. | |
| 2013/0190638 A1 | 7/2013 | Chon et al. | |

OTHER PUBLICATIONS

International Application No. PCT/US2014/070165 International Search Report and Written Opinion dated Apr. 17, 2015.

* cited by examiner

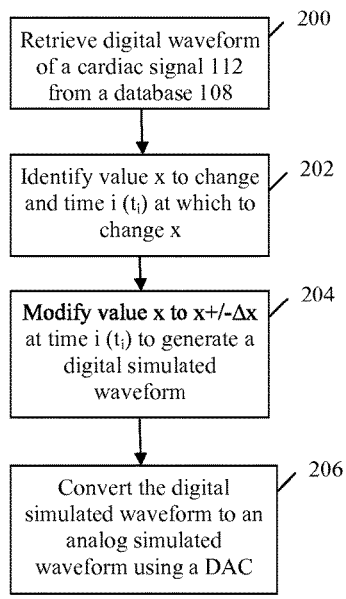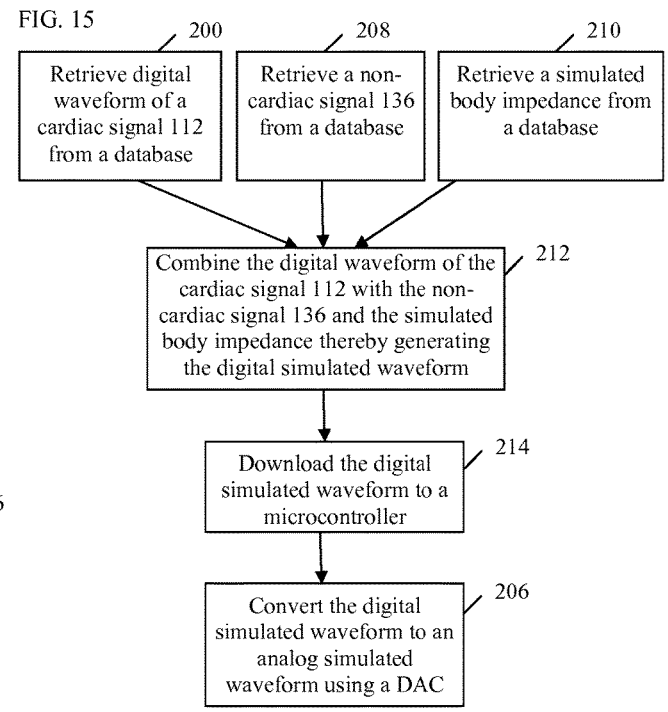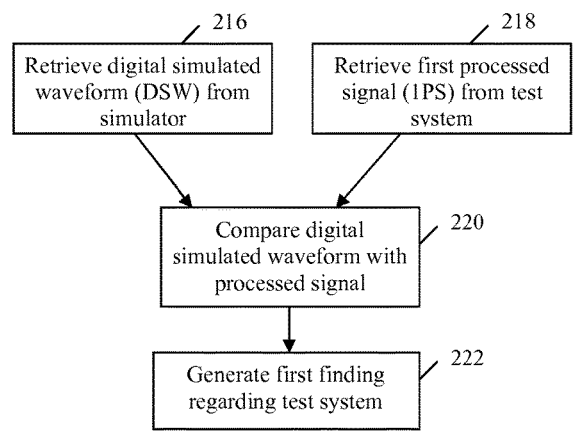

SYSTEMS AND METHODS FOR EVALUATION OF ELECTROPHYSIOLOGY SYSTEMS

CROSS-REFERENCE

This application is filed pursuant to 35 U.S.C. § 371 as a United States National Phase Application of International Application No. PCT/US2014/070165 entitled "SYSTEMS AND METHODS FOR EVALUATION OF ELECTROPHYSIOLOGY SYSTEMS" filed Dec. 12, 2014, which claims benefit of U.S. Provisional Patent Application Ser. No. 61/915,451, filed Dec. 12, 2013, the content of which each application is explicitly incorporated herein by reference in its entirety.

BACKGROUND OF THE INVENTION

Electrophysiology, also referred to Cardiac Electrophysiology, Clinical Cardiac Electrophysiology, and/or Arrhythmia Services is a branch of the medical specialty of clinical cardiology that studies and treats rhythm disorders of the heart. Experts in this field are typically Cardiologists who are referred to commonly as electrophysiologists. These experts are trained in the mechanism, function, and performance of the electrical activities of the heart, and work closely with other cardiologists and cardiac surgeons to assist or guide therapy for heart rhythm disturbances such as arrhythmias. They are often trained to perform interventional and surgical procedures to treat cardiac arrhythmia.

Typically, Electrophysiology evaluations or studies include the insertion of pacing and recording electrodes either in the esophagus (intra-esophageal) or, through blood vessels, directly into the heart chambers (intra-cardiac) in order to measure electrical properties of the heart and, in the case of intra-cardiac electrophysiology studies, to electrically stimulate it in the attempt to induce arrhythmias for diagnostic purposes ("programmed electrical stimulation").

SUMMARY OF THE INVENTION

Provided herein are devices, systems, and methods that provide objective assessments of electrophysiology (EP) recorders and mapping systems' accuracy in the acquisition of cardiac signals. During electrophysiology (EP) studies, cardiac signals are obtained by attaching multiple electrodes to a patient's chest and limbs for surface electrocardiograms (ECG), and by inserting catheter(s) inside the patient's heart for intracardiac (IC) electrogram recordings. Cardiac signals are small and, therefore, require amplification so they can become visible for physicians to interpret and ultimately make clinical decisions. This is achieved by connecting the recording electrodes to an amplifier—an integral part of every EP recorder and mapping system. However, both wanted cardiac and unwanted spurious signals are picked up by the recording electrodes and will be amplified. The main spurious signals that hamper the acquisition process are baseline wander, noise and artifacts. Baseline wander causes cardiac signals to shift from the isoelectric line. Noise is usually manifested in recordings as a thick line masking the signal of interest—it represents a combination of various unwanted signals that are generated by the patient's body and the recording environment. In some cases, the noise signal can be as big, or bigger, than the signal carrying the cardiac information. Artifacts come from the patient's body movements, bad or loose connections of electrodes to skin or cardiac tissue, the recording environment, and various other sources. In order for the cardiac signals to be interpreted accurately by the physician, baseline wander, noise and artifacts must be minimized.

Provided herein is an electrophysiology simulator (EP simulator or simulator, herein) comprising a database connection to a database, wherein the database comprises at least one cardiac signal, and at least one or more of a simulated body impedance, a cardiac feature, and a non-cardiac signal; first circuitry configured to alter the cardiac signal by combining a digital waveform of the cardiac signal or an analog waveform of the cardiac signal with the simulated body impedance, the non-cardiac signal, or a combination thereof, thereby generating a digital simulated waveform or an analog simulated waveform; a D/A converter configured to convert the digital simulated waveform to the analog simulated waveform; a test system connection configured to couple the simulator to a first test system; a first evaluator connection configured to couple the simulator to an evaluator; and second circuitry configured to provide to the evaluator: the digital waveform or analog waveform of the cardiac signal, and information about whichever simulated body impedance, cardiac feature, and/or non-cardiac signal was used to generate the analog simulated waveform or the digital simulated waveform. Note that the test system connection is called this only to differentiate it from other connections such as the database connection 110 between the database and a computer or between the database and the simulator, or such as the simulator connection 116 which may be between a computer and a simulator, or such as the first evaluator connection which may be between the evaluator and the simulator or between the evaluator and the database or between the evaluator and the database, or such as the second evaluator connection which may be between the first test system and an evaluator.

In some embodiments, the non-cardiac signal comprises a noise signal, a baseline wander signal, or an artifact signal.

In some embodiments, the cardiac signal comprises an intracardiac electrogram, a surface electrocardiogram, or a test signal. In some embodiments, the cardiac signal comprises one or more of an electrocardiogram, a unipolar electrogram, and a bipolar electrogram. In some embodiments, the cardiac signal comprises a cardiac activation map or data necessary to generate the cardiac activation map.

In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the simulator comprises the database.

In some embodiments, the first test system comprises at least one of a recorder and a mapping system.

In some embodiments, the test system connection couples to a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector. In some embodiments, the simulator comprises the junction box.

In some embodiments, the device simulator comprises third circuitry configured to combine the digital waveform of the cardiac signal, the analog waveform of the cardiac signal, the digital simulated waveform or the analog simulated waveform with the cardiac feature. In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), non-specific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this could be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

In some embodiments, the information comprises how the cardiac signal was altered. In some embodiments, the information comprises the digital waveform or analog waveform of the cardiac signal. In some embodiments, the information further comprises the simulated body impedance and/or the non-cardiac signal used to generate the analog simulated waveform or the digital simulated waveform. In some embodiments, the information comprises the digital waveform or analog waveform of the cardiac signal as combined with the cardiac feature. In some embodiments, the information further comprises the simulated body impedance and/or the non-cardiac signal used to generate the analog simulated waveform or the digital simulated waveform.

In some embodiments, the simulator comprises controls that allow a user to choose or provide the cardiac signal to be altered choose or provide the simulated body impedance, the non-cardiac signal, and/or the combination thereof that is used to alter the digital waveform or the analog waveform of the cardiac signal, and/or choose the amount by which the cardiac signal is altered by such body impedance, non-cardiac signal, and/or combination thereof.

In some embodiments, the simulator comprises controls that allow a user to choose or provide the cardiac signal to be altered, choose or provide the simulated body impedance, the cardiac feature, the non-cardiac signal, and/or the combination thereof that is used to alter the digital waveform or the analog waveform of the cardiac signal, and/or choose the amount by which the cardiac signal is altered by such body impedance, cardiac feature, non-cardiac signal, and/or combination thereof.

In some embodiments, the simulator comprises circuitry that determines for a user which cardiac signal from the database will be altered which simulated body impedance, non-cardiac signal, and/or combination thereof will be used to alter the digital waveform or the analog waveform of the cardiac signal, and/or the amount by which the cardiac signal is altered by such body impedance, non-cardiac signal, and/or combination thereof.

In some embodiments, the simulator comprises circuitry that determines for a user which cardiac signal from the database will be altered which simulated body impedance, cardiac feature, non-cardiac signal, and/or combination thereof will be used to alter the digital waveform or the analog waveform of the cardiac signal, and/or the amount by which the cardiac signal is altered by such body impedance, cardiac feature, non-cardiac signal, and/or combination thereof.

Provided herein is a method of simulating an analog electrophysiologic signal comprising providing a digital waveform of a cardiac signal or an analog waveform of the cardiac signal, wherein the cardiac signal comprises an intracardiac electrogram, a surface electrocardiogram, or a test signal from a database of cardiac signals, altering the cardiac signal by combining either the digital waveform or the analog waveform with a simulated body impedance, a non-cardiac signal, or a combination thereof, thereby generating a digital simulated waveform or an analog simulated waveform, converting the digital simulated waveform, if generated, to the analog simulated waveform, providing to a first test system the analog simulated waveform, providing to the evaluator the analog simulated waveform and/or the digital simulated waveform, and information about the digital waveform or an analog waveform of the cardiac signal, and/or whichever simulated body impedance, cardiac feature, and/or non-cardiac signal was used to generate the analog simulated waveform or the digital simulated waveform.

In some embodiments, the non-cardiac signal comprises a noise signal, a baseline wander signal, or an artifact signal. In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the simulator comprises the database. In some embodiments, the first test system comprises at least one of a recorder and a mapping system.

In some embodiments, providing the analog simulated waveform comprises providing a coupling that can be used to couple a simulator that generated the analog simulated waveform to a junction box and providing a coupling that can be used to couple the junction box to the first test system. In some embodiments, the coupling couples the junction box to the first test system couples the junction box to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector.

In some embodiments, the method comprises combining the cardiac signal with the non-cardiac signal. In some embodiments, the method comprises combining the digital waveform of the cardiac signal, the analog waveform of the cardiac signal, the digital simulated waveform or the analog simulated waveform with the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supravetricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), nonspecific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this could be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is $</=20$ times the minimum detectability limit of the first test system. In some embodiments, the detectability boundary is $</=10$ times the minimum detectability limit of the first test system. In some embodiments, the detectability boundary is $</=5$ times the minimum detectability limit of the first test system. In some embodiments, the detectability boundary is $</=3$ times the minimum detectability limit of the first test system. In some embodiments, the detectability boundary is $</=2$ times the minimum detectability limit of the first test system. The term "about" as used herein with regard to the detectability limit refers to variability of +/−10%, +/−25%, or +/−50%, depending on the embodiment.

In some embodiments, the information comprises how the cardiac signal was altered. In some embodiments, the information comprises the digital waveform or analog waveform of the cardiac signal. In some embodiments, the information comprises the simulated body impedance, and/or the non-cardiac signal used to generate the analog simulated waveform or the digital simulated waveform. In some embodiments, the information comprises the digital waveform or analog waveform of the cardiac signal as combined with the cardiac feature. In some embodiments, the information further comprises the simulated body impedance and/or the non-cardiac signal used to generate the analog simulated waveform or the digital simulated waveform.

In some embodiments, the method comprises providing controls that allow a user to choose or provide the cardiac signal to be altered choose or provide the simulated body impedance, the non-cardiac signal, and/or the combination thereof that is used to alter the digital waveform or the analog waveform of the cardiac signal, and/or choose the amount by which the cardiac signal is altered by such body impedance, non-cardiac signal, and/or combination thereof.

In some embodiments, the method comprises providing controls that allow a user to choose or provide the cardiac signal to be altered choose or provide the simulated body impedance, the cardiac feature, the non-cardiac signal, and/or the combination thereof that is used to alter the digital waveform or the analog waveform of the cardiac signal, and/or choose the amount by which the cardiac signal is altered by such body impedance, cardiac feature, non-cardiac signal, and/or combination thereof.

In some embodiments, the method comprises providing circuitry that determines for a user which cardiac signal from the database will be altered which simulated body impedance, non-cardiac signal, and/or combination thereof will be used to alter the digital waveform or the analog waveform of the cardiac signal, and/or the amount by which the cardiac signal is altered by such body impedance, non-cardiac signal, and/or combination thereof.

In some embodiments, the method comprises providing circuitry that determines for a user which cardiac signal from the database will be altered which simulated body impedance, cardiac feature, non-cardiac signal, and/or combination thereof will be used to alter the digital waveform or the analog waveform of the cardiac signal, and/or the amount by which the cardiac signal is altered by such body impedance, cardiac feature, non-cardiac signal, and/or combination thereof.

Provided herein is a signal processing evaluator comprising: a digital waveform of a cardiac signal or an analog waveform of the cardiac signal, a first processed signal received from a first test system, wherein the first processed signal is the result of digital processing of an analog simulated waveform by the first test system, wherein the analog simulated waveform was generated by combining the digital waveform of the cardiac signal or the analog waveform of the cardiac signal with a simulated body impedance, a non-cardiac signal, and/or a combination thereof, and third circuitry that compares the digital waveform of the cardiac signal or the analog waveform of the cardiac signal to the first processed signal and generates a first finding evaluating the first test system.

In some embodiments, the first finding depicts or describes how closely matched the first processed signal is to the digital waveform of the cardiac signal or to the analog waveform of the cardiac signal.

In some embodiments, the evaluator comprises information about the simulated body impedance, the non-cardiac signal, and/or the combination thereof that was used to generate the analog simulated waveform.

In some embodiments, the evaluator comprises second circuitry that compares the first finding to a second finding in order to evaluate the first test system, or in order to compare a first test system to a second test system. In some embodiments, the second finding depicts or describes how closely matched a second processed signal that is the result of digital processing of the analog simulated waveform by a second test system is to the digital waveform of the cardiac signal or to the analog waveform, and generates an evaluation regarding which of the first test system and the second test system better processes the analog simulated waveform.

In some embodiments, the first finding expresses the effectiveness of the first test system in reproducing the digital waveform of the cardiac signal or the analog waveform of the cardiac signal from the analog simulated waveform.

In some embodiments, the first circuitry is configured to compare a second digital waveform of a second cardiac signal or second analog waveform of the second cardiac signal to a second processed signal. In some embodiments, the second processed signal is a result of digital processing of a second analog simulated waveform by the first test system, wherein the second analog simulated waveform is generated based on the second digital waveform of the second cardiac signal or the second analog waveform of the cardiac signal and a second simulated body impedance, a second non-cardiac signal, and/or a combination thereof.

In some embodiments, the digital waveform of the cardiac signal or the analog waveform of the cardiac signal comprises a cardiac feature. In some embodiments, the first finding expresses how well the first test system preserves the cardiac feature in the first processed signal as compared to the digital waveform of the cardiac signal or to the analog waveform of the cardiac signal.

In some embodiments, the evaluator comprises information about the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), nonspecific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this could be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

In some embodiments, the first finding expresses how well the first test system removes the non-cardiac signal from the analog simulated waveform. In some embodiments, the first finding expresses how well the first test system removes the simulated body impedance from the analog simulated waveform. In some embodiments, the first circuitry is configured to assess the first processed signal and the digital waveform of the cardiac signal or the analog waveform of the cardiac signal in the time domain, frequency domain, or a combination thereof.

In some embodiments, the non-cardiac signal comprises a noise signal, a baseline wander signal, or an artifact signal. In some embodiments, cardiac signal comprises an intracardiac electrogram, a surface electrocardiogram, or a test signal. In some embodiments, the test signal comprises an Electrocardiograph Committee (EC) standard waveform. In some embodiments, the EC standard waveform is a standard for testing the recorder or the mapping system as defined by ANSI or AAMI. In some embodiments, the cardiac signal comprises one or more of an electrocardiogram, a unipolar electrogram, and a bipolar electrogram. In some embodiments, the first processed signal comprises a reconstructed cardiac activation map or data necessary to generate the reconstructed cardiac activation map.

In some embodiments, the first test system comprises at least one of a recorder and a mapping system. In some embodiments, the recorder comprises an electrophysiology recorder. In some embodiments, the mapping system comprises an electrophysiology mapping system. In some embodiments, the first test system comprises an analog filter or a digital filter or a combination thereof configured to process the analog simulated waveform in order to generate the first processed signal.

In some embodiments, the evaluator comprises an evaluator connection to the first test system. In some embodiments, the evaluator comprises a database or a database connection to a database, wherein the database comprises the cardiac signal, and at least one of the simulated body impedance and the non-cardiac signal. In some embodiments, the database comprises a cardiac feature.

In some embodiments, the evaluator comprises first circuitry configured to alter the cardiac signal by combining the digital waveform of the cardiac signal or the analog waveform of the cardiac signal with the simulated body impedance, the non-cardiac signal, or a combination thereof, thereby generating a digital simulated waveform or an analog simulated waveform. In some embodiments, the evaluator comprises a D/A converter configured to convert the digital simulated waveform to the analog simulated waveform. In some embodiments, the evaluator comprises the database.

In some embodiments, the first test system comprises at least one of a recorder and a mapping system. In some embodiments, the test system connection couples to a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector. In some embodiments, the simulator comprises the junction box.

Provided herein is a method comprising: providing a signal processing evaluator to a user, wherein the evaluator comprises a digital waveform of a cardiac signal or an analog waveform of the cardiac signal, a first processed signal received from a first test system, wherein the first processed signal is the result of digital processing of an analog simulated waveform by the first test system, wherein the analog simulated waveform was generated by combining the digital waveform of the cardiac signal or the analog waveform of the cardiac signal with a simulated body impedance, a non-cardiac signal, and/or a combination thereof, and third circuitry that compares the digital waveform of the cardiac signal or the analog waveform of the cardiac signal to the first processed signal and generates a first finding evaluating the first test system.

Provided herein is a method comprising: receiving a first processed signal from a first test system, wherein the first processed signal is the result of digital processing of an analog simulated waveform by the first test system, wherein the analog simulated waveform was generated by combining a digital waveform of a cardiac signal or an analog waveform of the cardiac signal with a simulated body impedance, a non-cardiac signal, and/or a combination thereof, comparing the digital waveform of the cardiac signal or the analog waveform of the cardiac signal to the first processed signal, generating a first finding that evaluates the first test system, and providing the first finding to a user.

In some embodiments, the first finding depicts or describes how closely matched the first processed signal is to the digital waveform of the cardiac signal or to the analog waveform of the cardiac signal.

In some embodiments, the method comprises providing information about the simulated body impedance, the non-cardiac signal, and/or the combination thereof that was used to generate the analog simulated waveform. In some embodiments, the method comprises comparing the first finding to a second finding evaluating a second test system. In some embodiments, the second finding depicts or describes how closely matched a second processed signal that is the result of digital processing of the analog simulated waveform by a second test system is to the digital waveform of the cardiac signal or to the analog waveform, and generates an evaluation regarding which of the first test system and the second test system better processes the analog simulated waveform.

In some embodiments, the first finding expresses the effectiveness of the first test system in reproducing the digital waveform of the cardiac signal or the analog waveform of the cardiac signal from the analog simulated waveform.

In some embodiments, the method comprises comparing a second digital waveform of a second cardiac signal or second analog waveform of the second cardiac signal to a second processed signal. In some embodiments, the second processed signal is a result of digital processing of a second analog simulated waveform by the first test system, wherein the second analog simulated waveform is generated based on the second digital waveform of the second cardiac signal or the second analog waveform of the cardiac signal and a second simulated body impedance, a second non-cardiac signal, and/or a combination thereof.

In some embodiments, the digital waveform of the cardiac signal or the analog waveform of the cardiac signal comprises a cardiac feature. In some embodiments, the first finding expresses how well the first test system preserves the cardiac feature in the first processed signal as compared to the digital waveform of the cardiac signal or to the analog waveform of the cardiac signal.

In some embodiments, the method comprises providing information about the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), non-specific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI)

(fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this could be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is $</=20$ times the minimum detectability limit of the first test system. In some embodiments, the detectability boundary is $</=10$ times the minimum detectability limit of the first test system. In some embodiments, the detectability boundary is $</=5$ times the minimum detectability limit of the first test system. In some embodiments, the detectability boundary is $</=3$ times the minimum detectability limit of the first test system. In some embodiments, the detectability boundary is $</=2$ times the minimum detectability limit of the first test system. The term "about" as used herein with regard to the detectability limit refers to variability of +/−10%, +/−25%, or +/−50%, depending on the embodiment.

In some embodiments, the first finding expresses how well the first test system removes the non-cardiac signal from the analog simulated waveform. In some embodiments, the first finding expresses how well the first test system removes the simulated body impedance from the analog simulated waveform.

In some embodiments, the method comprises assessing the first processed signal and the digital waveform of the cardiac signal or the analog waveform of the cardiac signal in the time domain, frequency domain, or a combination thereof.

In some embodiments, the non-cardiac signal comprises a noise signal, a baseline wander signal, or an artifact signal. In some embodiments, the cardiac signal comprises an intracardiac electrogram, a surface electrocardiogram, or a test signal. In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the first test system comprises at least one of a recorder and a mapping system. In some embodiments, the recorder comprises an electrophysiology recorder. In some embodiments, the mapping system comprises an electrophysiology mapping system. In some embodiments, the first test system comprises an analog filter or a digital filter or a combination thereof configured to process the analog simulated waveform in order to generate the first processed signal. In some embodiments, the cardiac signal comprises one or more of an electrocardiogram, a unipolar electrogram, and a bipolar electrogram. In some embodiments, the first processed signal comprises a reconstructed cardiac activation map or data necessary to generate the reconstructed cardiac activation map.

In some embodiments, the method comprises generating the analog simulated waveform by combining the digital waveform of the cardiac signal or the analog waveform of the cardiac signal with the simulated body impedance, the non-cardiac signal, or the combination thereof. In some embodiments, the method comprises converting a digital simulated waveform of the digital waveform of the cardiac signal as combined with the simulated body impedance, the non-cardiac signal, or the combination thereof to the analog simulated waveform. In some embodiments, the method comprises receiving the one or more of the digital waveform of the cardiac signal, the analog waveform of the cardiac signal, the simulated body impedance, the non-cardiac signal, or a cardiac feature from a database.

In some embodiments, the first test system comprises at least one of a recorder and a mapping system.

In some embodiments, the method comprises providing a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 14 depicts a flow chart of an embodiment of a modification of a waveform by a simulator. Other examples and embodiments are possible, based on the description herein, at least.

FIG. 15 depicts an embodiment of a digital waveform of a cardiac signal retrieved from a database.

FIG. 16 depicts an embodiment of a method of evaluating how well a test system filters simulated body impedance and non-cardiac signals from an analog simulated signal, and preserves certain cardiac features or modifications to a cardiac signal.

DETAILED DESCRIPTION OF THE INVENTION

Provided herein are devices, systems, and methods that provide objective assessments of electrophysiology (EP) recorders and mapping systems' accuracy in the acquisition of cardiac signals. During electrophysiology (EP) studies, cardiac signals are obtained by attaching multiple electrodes to a patient's chest and limbs for surface electrocardiograms (ECG), and by inserting catheter(s) inside the patient's heart for intracardiac (IC) electrogram recordings. Cardiac signals are small and, therefore, require amplification so they can become visible for physicians to interpret and ultimately make clinical decisions. This is achieved by connecting the recording electrodes to an amplifier—an integral part of every EP recorder and mapping system. However, both wanted cardiac and unwanted spurious signals are picked up by the recording electrodes and will be amplified. The main spurious signals that hamper the acquisition process are baseline wander, noise and artifacts. Baseline wander causes cardiac signals to shift from the isoelectric line. Noise is usually manifested in recordings as a thick line masking the signal of interest—it represents a combination of various unwanted signals that are generated by the patient's body and the recording environment. In some cases, the noise signal can be as big, or bigger, than the signal carrying the cardiac information. Artifacts come from the patient's body movements, bad or loose connections of electrodes to skin or cardiac tissue, the recording environment, and various other sources. In order for the cardiac signals to be interpreted accurately by the physician, baseline wander, noise and artifacts can be minimized by evaluating the test system using the evaluator described herein in order to determine if the test system can sufficiently remove such non-cardiac signals and body impedance without removing certain features of the cardiac signal (called cardiac features, herein).

To form clinical decisions, physicians evaluate and measure different parameters of electrocardiogram and electrogram waveforms. These parameters typically include: the P wave, a QRS complex, a T wave, a U wave, and the isoelectric line.

As waveforms represent underlying disease, differential diagnostic decisions are made based on changes in shape and parameter values at certain points. Values labeled as "normal" or within certain boundaries will not require clinical intervention, while changes in waveforms that are disease-related may require clinical intervention.

Figure 4A:
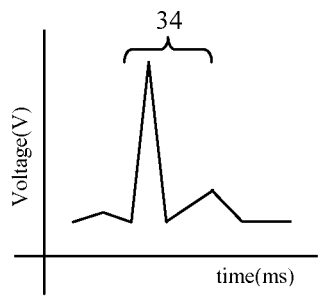
FIGS. 4A and 4B depict an embodiment of a shortened QT and a prolonged QT interval, respectively, wherein the x-axis is time and the y-axis is voltage.
Figure 4B:
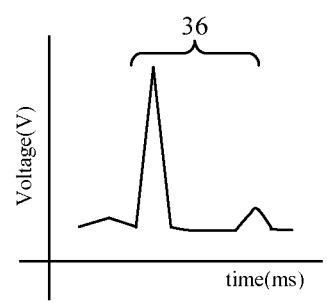
Figure 5:
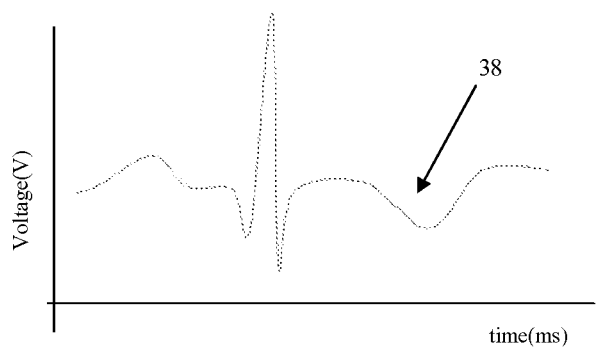
FIG. 5 depicts an embodiment of an inverted T wave wherein the x-axis is time and the y-axis is voltage.
Figure 6:
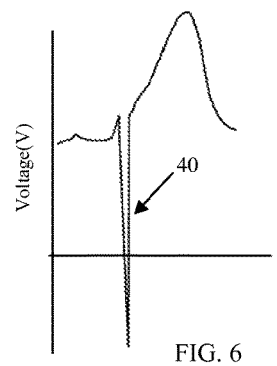
FIG. 6 depicts an embodiment of a hyperacute T wave wherein the T wave is prominent and pointed, and wherein x-axis is time and the y-axis is voltage.
Figure 7:
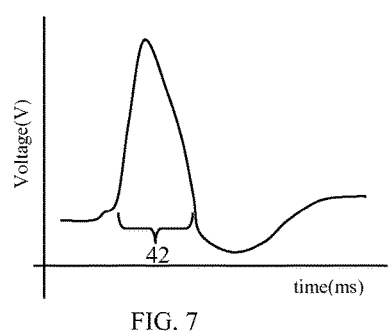
FIG. 7 depicts an embodiment of a wide QRS complex wherein the x-axis is time and the y-axis is voltage.
Figure 8:
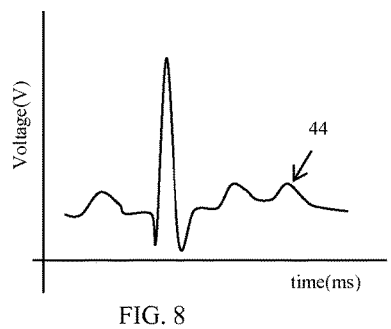
FIG. 8 depicts an embodiment of a prominent U wave wherein the x-axis is time and the y-axis is voltage.

For non-limiting example, waveforms depicting a shortened or prolonged QT interval can indicate hypercalcemia, hyperkalemia, hypocalcemia, certain drug effects, or certain genetic abnormalities. FIG. 4A and FIG. 4B depicts a shortened QT interval 55 and a prolonged QT interval 56, respectively, where the x-axis is time and the y-axis is voltage. Waveforms depicting a flattened or inverted T wave can indicate coronary ischemia, hypokalemia, left ventricular hypertrophy, digoxin effect, or certain drug effects. FIG. 5 depicts an inverted T wave where the x-axis is time and the y-axis is voltage. Waveforms depicting hyperacute T waves can indicate acute myocardial infarction. FIG. 6 depicts a hyperacute T wave where the T wave is prominent and pointed, and where x-axis is time and the y-axis is voltage. Waveforms depicting a wide QRS complex can indicate hyperkalemia. FIG. 7 depicts a wide QRS complex where the x-axis is time and the y-axis is voltage. Waveforms depicting a prominent U wave can indicate hyperkalemia. FIG. 8 depicts a prominent U wave where the x-axis is time and the y-axis is voltage.

Figure 9:
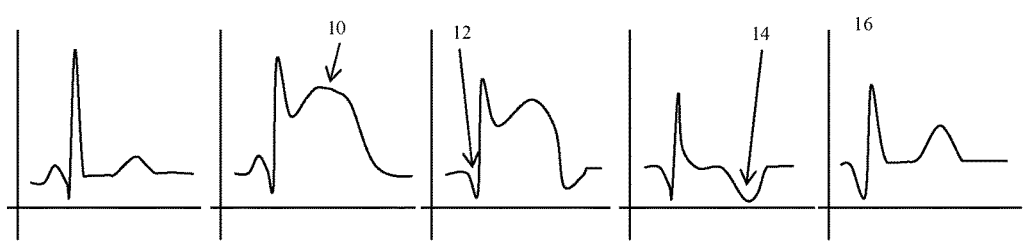
FIG. 9 depicts an embodiment of a typical progression of myocardial infarction represented by a sequence of ST elevation, Q wave formation, T wave inversion, and normalization with a persistent Q wave.
Figure 10:
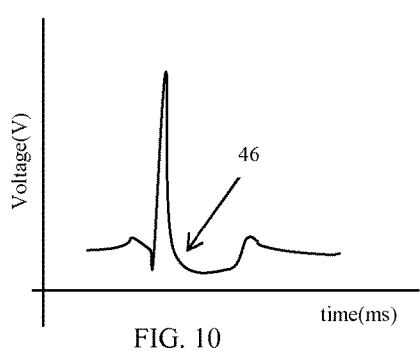
FIG. 10 depicts an embodiment of a typical characterization of digoxin intoxication represented by a deeply curved ST wave.
Figure 11:
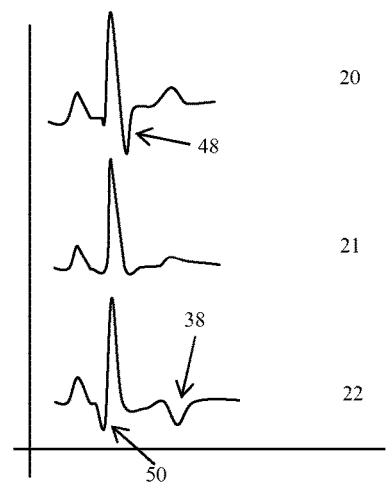
FIG. 11 depicts an embodiment of a typical characterization of pulmonary embolism represented by S-waves in lead I, Q-waves in lead III, and inverted T-waves in lead III of a surface electrode 12-lead ECG.
Figure 12:
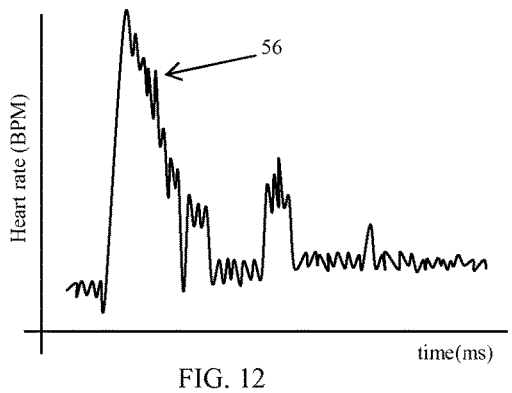
FIG. 12 depicts an embodiment of a typical characterization of epileptic seizures represented by abrupt changes in heart rate.

Certain other diseases are indicated by specific patterns in ECG recordings. Myocardial infarction is typically characterized by an ST elevation, Q wave formation, T wave inversion, and normalization with a persistent Q wave (shown in FIG. 9). Digoxin intoxication is typically characterized by a deep curved ST wave (shown in FIG. 10). Pulmonary embolism is typically characterized by S-waves in lead I, Q-waves in lead III, and inverted T-waves in lead III (shown in FIG. 11). Epileptic seizures are typically characterized by abrupt changes in heart rate (shown in FIG.

Figure 13:
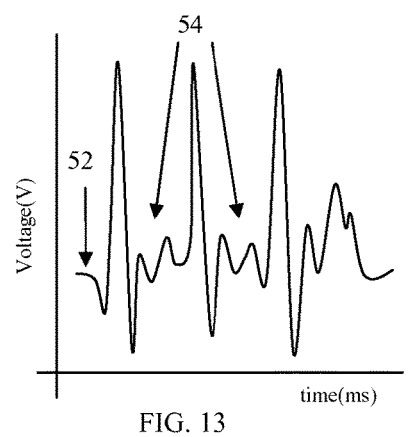
FIG. 13 depicts an embodiment of a typical characterization of atrial fibrillation represented by the absence of P-waves and absence of the iso-electric line.

12). Atrial fibrillation is typically characterized by absence of P-waves and absence of the isoelectric line (shown in FIG. 13).

Test systems (such as EP recorders and mapping systems) use a combination of analog and digital filters to remove noise, baseline wander and artifact signals, which may be called non-cardiac signals herein. The main problem with this approach is that this technique not only partially removes spurious signals, but this process also alters the true signal morphology and the content of the original cardiac information. The shape and amplitude of electrocardiograms, unipolar electrograms, bipolar electrograms, and, consequently, the reconstructed cardiac activation maps, are influenced not only by electrophysiological and structural characteristics of the myocardial tissue involved, but with characteristics of the recording system used for signal acquisition.

Artifacts, or artifact signals, may be physiological and/or non-physiological. Physiological artifact signals include, in certain embodiments, signals from muscles other than the heart that appear as narrow, rapid spikes associated with muscle movement, as well as the skin which produces voltage of several millivolts that can be generated by stretching the epidermis. Non-physiological artifact signals include, in certain embodiments, the 60 Hz energy from an electrical wall source which is received in the lead wires and by the patient, the offset potential voltage that is stored by the electrode, and breaks in the wires and connections between the electrode and the monitor.

Amplitude and morphology of ECG and IC signals are significantly affected by filters used to remove the unwanted signals. As cardiac signals (generated by the human body) are unknown, it is difficult to objectively evaluate the effect of various analog and digital signal processing schemes used to remove unwanted signals during signal acquisition. There are a number of amplitude and interval measurements taken on the acquired signals during an EP study. In order to make proper clinical decisions, it is imperative that the recording system faithfully acquires spatiotemporal characteristics of surface ECG and intracardiac electrograms. If the EP recording system generates "phantom" data which mimics a cardiac disease, it can cause the physician to make a wrong clinical decision.

Simulator

The simulator described herein can change the waveshapes of a cardiac signal to correspond to various waveshapes of diseases. It can also or alternatively change the waveshape of the cardiac signal in a fine-tuned manner to result in a small change in waveshape, which may or may not be clinically abnormal. This fine tuning may allow the evaluator described herein to determine if a particular test system can detect the finely changed waveform and detect smaller changes to the waveform relevant to particular disease states that are associated with small changes, or are in the early stages of development, or are typically undetectable by standard test systems because these test systems filter out small changes and do not flag or indicate such small changes as abnormal.

Provided herein is an electrophysiology simulator comprising a database connection to a database, wherein the database comprises at least one cardiac signal, and at least one or more of a simulated body impedance, a cardiac feature, and a non-cardiac signal; first circuitry configured to alter the cardiac signal by combining a digital waveform of the cardiac signal or an analog waveform of the cardiac signal with the simulated body impedance, the non-cardiac signal, or a combination thereof, thereby generating a digital simulated waveform or an analog simulated waveform; a D/A converter configured to convert the digital simulated waveform to the analog simulated waveform; a test system connection configured to couple the simulator to a first test system; a first evaluator connection configured to couple the simulator to an evaluator; and second circuitry configured to provide to the evaluator: the digital waveform or analog waveform of the cardiac signal, and information about whichever simulated body impedance, cardiac feature, and/or non-cardiac signal was used to generate the analog simulated waveform or the digital simulated waveform.

In some embodiments, the non-cardiac signal comprises a noise signal, a baseline wander signal, or an artifact signal.

In some embodiments, the cardiac signal comprises an intracardiac electrogram, a surface electrocardiogram, or a test signal. In some embodiments, the cardiac signal comprises one or more of an electrocardiogram, a unipolar electrogram, and a bipolar electrogram. In some embodiments, the cardiac signal comprises a cardiac activation map or data necessary to generate the cardiac activation map.

In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the simulator comprises the database.

In some embodiments, the first test system comprises at least one of a recorder and a mapping system.

In some embodiments, the test system connection couples to a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector. In some embodiments, the simulator comprises the junction box.

In some embodiments, the device simulator comprises third circuitry configured to combine the digital waveform of the cardiac signal, the analog waveform of the cardiac signal, the digital simulated waveform or the analog simulated waveform with the cardiac feature. In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), non-specific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of an cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this could be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

Example 1

Characteristics of the digitized waveforms in time domain can be described with two parameters: time (ti (i=1, n)) and value x at that specific point in time. Time can be expressed in seconds or fraction of seconds. Usually, t1 denotes the start of the recording, and ti represents the data point during the recording, while $\Delta t$ is time between two successive samples. Value x, at a given point in time ti, can be expressed in different units (voltage, current, pressure . . . etc.). This depends on what type of transducer is used to transfer physiological parameters into electrical signals.

For every position ti on the digitized waveform, the x value can be modified. This process involves identification of a time point at ti and changing the parameter value from x to x±$\Delta$x. $\Delta$x represents the value of the desired change expressed in p×q, where q is the lower end of resolution (for example when x is voltage, the resolution q is the LSB or least significant bit) of the A/D converter (function of resolution and full scale range) and p is an integer that is a best fit to achieve desired change. The A/D converter (also called an "ADC") may be in the test system itself, thus the Simulator x value may be modified based on the minimum resolution of the (lower end) of resolution of the test system.

FIG. 14 depicts a flow chart of an example modification of a waveform by a simulator. Other examples and embodiments are possible, based on the description herein, at least. In step A of FIG. 14, a simulator retrieves a digital waveform of a cardiac signal from a database. That is, a digital waveform of a cardiac signal may be provided to the simulator from a database. The database may be part of the simulator or remotely existing (for example in a computer workstation or handheld device). In Step B of FIG. 14, a user decides and identifies the parameter value x at a particular time (denoted as $t_i$) that they wish to change. Alternatively the simulator or computer program at a computer or workstation may automatically choose such value and time, depending on a particular disease that may be of interest, or based on the limits of the test system, or based on another boundary determination, or based on a user input. The digital value x at time i ($t_i$) in Step C of FIG. 14 is then altered by a delta x ($\Delta$x) at the time point $t_i$. This may be repeated any number of times for the value x at different times in order to change a waveform shape or amplitude or other aspect, or a single change may be made in order to evaluate the test system. Other values may alternatively or additionally be changed at the same time ($t_i$) or at different times. The choice of the change of x ($\Delta$x) may be based on the resolution of the test system itself, or on the resolution of the A/D converter used in the test system. That is, the value of the desired change expressed in p×q, where q is the lower end of resolution (for example when x is voltage, the resolution q is the LSB or least significant bit) of the A/D converter (function of resolution and full scale range) and p is an integer that is a best fit to achieve desired change. The A/D converter (also called an "ADC") is part of the test system itself, thus the simulator x value may be modified based on the minimum resolution of the (lower end) of resolution of the test system.

In common ADCs, the LSB is the minimum change in voltage required to guarantee a change in the output code level. Thus, the resolution q of the ADC is equal to the LSB voltage.

The resolution of the ADC indicates the number of discrete values it can produce over the range of analog values. The resolution is usually expressed in bits and the number of discrete values available, or "levels", is a power of two. The values can represent the ranges from 0 to 255 (i.e. unsigned integer) or from −128 to 127 (i.e. signed integer), depending on the application.

The voltage resolution of an ADC is equal to its overall voltage measurement range divided by the number of discrete values: $Q=E_{FSR}/(2^M-1)$ wherein M is the ADC's resolution in bits and $E_{FSR}$ is the full scale voltage range (also called 'span'). $E_{FSR}$ is given by $E_{FSR}=V_{RefHi}-V_{RefLow}$ wherein $V_{RefHi}$ and $V_{RefLow}$ are the upper and lower extremes, respectively, of the voltages that can be coded. Normally, the number of voltage intervals is given by $N=(2^M-1)$ wherein M is the ADC's resolution in bits. That is, one voltage interval is assigned in between two consecutive code levels. In practice, the useful resolution of a converter is limited by the best signal-to-noise ratio (SNR) that can be achieved for a digitized signal. An ADC can resolve a signal to only a certain number of bits of resolution, called the effective number of bits (ENOB). One effective bit of resolution changes the signal-to-noise ratio of the digitized signal by 6 dB, if the resolution is limited by the ADC. If a preamplifier has been used prior to A/D conversion, the noise introduced by the amplifier can be an important contributing factor towards the overall signal to noise ratio (SNR).

Once the value of x at time i ($t_i$) is changed and any other changes to the same or another value are complete (if any), in Step D of FIG. 14 the digital waveform is converted by a D/A converter ("DAC") and an analog simulated waveform is generated.

Prior to or after this D/A conversion, a simulated impedance or a non-cardiac signal may be combined with the digital simulated waveform or to the analog simulated waveform, respectively. The purpose of this is to simulate the non-cardiac and impedance that may occur in real EC recordings which the test systems are designed to try to filter in order to generate a processed signal that still identifies and captures the change in value x ($\Delta$x) at time i (and/or any other changes) that were introduced to the cardiac signal from the database.

In some embodiments the retrieving, identifying of the value x to change and the time i at which to change it and the modification of the value x is done at a computer that is coupled to a DAC. The modified digital simulated waveform is thus downloaded to a microcontroller comprising circuitry that can convert the digital simulated waveform to an analog simulated waveform, or can combine the digital simulated waveform with a non-cardiac signal or a simulated body impedance, or other signal. Alternatively, prior to downloading, the digital simulated waveform may be further altered by a non-cardiac signal or a simulated body impedance or another signal and subsequently downloaded to the microcontroller that can load the digital simulated waveform (altered thereby) into the DAC. The DAC may be coupled to a junction box, as described herein, or to the test system directly or indirectly through a catheter or by another connection source (cord, remote, wifi, etc.)

In some embodiments, the simulator converts a digital waveform, such as the digital simulated waveform, which could be the digital waveform of a cardiac signal either with or without an additional cardiac feature combined therewith and including a simulated impedance or a non-cardiac signal, to an analog simulated waveform using a DAC. For non-limiting example, common types of electronic DACs include the following forms.

One example DAC is a pulse-width modulator, the simplest DAC type. A stable current or voltage is switched into a low-pass analog filter with a duration determined by the digital input code. This technique is often used for electric motor speed control, but has many other applications as well.

Another example DAC is an oversampling DAC or interpolating DAC such as the delta-sigma DAC, use a pulse density conversion technique. The oversampling technique allows for the use of a lower resolution DAC internally. A simple 1-bit DAC is often chosen because the oversampled result is inherently linear. The DAC is driven with a pulse-density modulated signal, created with the use of a low-pass filter, step nonlinearity (the actual 1-bit DAC), and negative feedback loop, in a technique called delta-sigma modulation. This results in an effective high-pass filter acting on the quantization (signal processing) noise, thus steering this noise out of the low frequencies of interest into the megahertz frequencies of little interest, which is called noise shaping. The quantization noise at these high frequencies is removed or greatly attenuated by use of an analog low-pass filter at the output (sometimes a simple RC low-pass circuit is sufficient). Most very high resolution DACs (greater than 16 bits) are of this type due to its high linearity and low cost. Higher oversampling rates can relax the specifications of the output low-pass filter and enable further suppression of quantization noise. Speeds of greater than 100 thousand samples per second (for example, 192 kHz) and resolutions of 24 bits are attainable with delta-sigma DACs. A short comparison with pulse-width modulation shows that a 1-bit DAC with a simple first-order integrator would have to run at 3 THz (which is physically unrealizable) to achieve 24 meaningful bits of resolution, requiring a higher-order low-pass filter in the noise-shaping loop. A single integrator is a low-pass filter with a frequency response inversely proportional to frequency and using one such integrator in the noise-shaping loop is a first order delta-sigma modulator. Multiple higher order topologies (such as MASH) are used to achieve higher degrees of noise-shaping with a stable topology.

Another example DAC is a binary-weighted DAC, which contains individual electrical components for each bit of the DAC connected to a summing point. These precise voltages or currents sum to the correct output value. This is one of the fastest conversion methods but suffers from poor accuracy because of the high precision required for each individual voltage or current. Such high-precision components are expensive, so this type of converter is usually limited to 8-bit resolution or less. One type of binary-weighted DAC is a switched resistor DAC which contains a parallel resistor network in which individual resistors are enabled or bypassed in the network based on the digital input. Another type of binary-weighted DAC is a switched current source DAC, from which different current sources are selected based on the digital input. Another type of binary-weighted is a switched capacitor DAC which contains a parallel capacitor network in which individual capacitors are connected or disconnected with switches based on the input.

Another example DAC is a R-2R ladder DAC, which is a binary-weighted DAC that uses a repeating cascaded structure of resistor values R and 2R. This improves the precision due to the relative ease of producing equal valued-matched resistors (or current sources). However, wide converters perform slowly due to increasingly large RC-constants for each added R-2R link.

Another example DAC is a Successive-Approximation or Cyclic DAC, which successively constructs the output during each cycle. Individual bits of the digital input are processed each cycle until the entire input is accounted for.

Another example DAC is a thermometer-coded DAC, which contains an equal resistor or current-source segment for each possible value of DAC output. An 8-bit thermometer DAC would have 255 segments, and a 16-bit thermometer DAC would have 65,535 segments. This is perhaps the fastest and highest precision DAC architecture but at the expense of high cost. Conversion speeds of more than 1 billion samples per second have been reached with this type of DAC.

Another example DAC is a Hybrid DACs, which use a combination of the above techniques in a single converter. Most DAC integrated circuits are of this type due to the difficulty of getting low cost, high speed and high precision in one device. One type of hybrid DAC is a segmented DAC, which combines the thermometer-coded principle for the most significant bits and the binary-weighted principle for the least significant bits. In this way, a compromise is obtained between precision (by the use of the thermometer-coded principle) and number of resistors or current sources (by the use of the binary-weighted principle). The full binary-weighted design means 0% segmentation, the full thermometer-coded design means 100% segmentation.

Most DACs, shown earlier in this list, rely on a constant reference voltage to create their output value. Alternatively, a multiplying DAC[1] takes a variable input voltage for their conversion. This puts additional design constraints on the bandwidth of the conversion circuit.

Example 2

FIG. 15 depicts an example wherein a digital waveform of a cardiac signal is retrieved from a database in Step 200. A non-cardiac signal is retrieved from a database in step 208, and alternatively, or additionally, a simulated body impedance is retrieved from a database in step 210. These signals are combined into a single waveform, by in some embodiments, combining the digital versions of each of these signals. In other embodiments, the digital waveform of the cardiac signal is combined with the non-cardiac signal. Additionally or alternatively to the non-cardiac signal, a cardiac feature may be combined with the digital waveform of the cardiac signal. This combination may then be combined with a simulated body impedance that simulates a signal passing through a body impedance circuit. The digital simulated waveform generated by the combination described herein or as depicted in step 212 of FIG. 15, may be downloaded to a microcontroller as noted in Step 214 of FIG. 15 which may comprise circuitry that loads the digital simulated waveform into a DAC, which generates an analog simulated signal as noted in Step 206 of FIG. 15.

In some embodiments, the simulator passes information to an evaluator that evaluates the test system's ability to filter certain body impedance (simulated impedance) or non-cardiac signals from the analog simulated signal. The information that the simulator provides to an evaluator may comprise how the cardiac signal was altered. In some embodiments, the information comprises the digital waveform or analog waveform of the cardiac signal. In some embodiments, the information comprises the cardiac signal. In some embodiments, the information further comprises the simulated body impedance and/or the non-cardiac signal used to generate the analog simulated waveform or the digital simulated waveform. In some embodiments, the information comprises the digital waveform or analog waveform of the cardiac signal as combined with the cardiac feature. In some embodiments, the information further comprises the simulated body impedance and/or the non-cardiac signal used to generate the analog simulated waveform or the digital simulated waveform.

In some embodiments, the simulator comprises controls that allow a user to choose or provide the cardiac signal to be altered choose or provide the simulated body impedance, the non-cardiac signal, and/or the combination thereof that is used to alter the digital waveform or the analog waveform of the cardiac signal, and/or choose the amount by which the cardiac signal is altered by such body impedance, non-cardiac signal, and/or combination thereof.

In some embodiments, the simulator comprises controls that allow a user to choose or provide the cardiac signal to be altered as well as choose or provide the simulated body impedance, the cardiac feature, the non-cardiac signal, and/or the combination thereof that is used to alter the digital waveform or the analog waveform of the cardiac signal, and/or choose the amount by which the cardiac signal is altered by such body impedance, cardiac feature, non-cardiac signal, and/or combination thereof.

In some embodiments, the simulator comprises circuitry that determines for a user which cardiac signal from the database will be altered, which simulated body impedance, non-cardiac signal, and/or combination thereof will be used to alter the digital waveform or the analog waveform of the cardiac signal, and/or the amount by which the cardiac signal is altered by such body impedance, non-cardiac signal, and/or combination thereof.

In some embodiments, the simulator comprises circuitry that determines for a user which cardiac signal from the database will be altered, which simulated body impedance, cardiac feature, non-cardiac signal, and/or combination thereof will be used to alter the digital waveform or the analog waveform of the cardiac signal, and/or the amount by which the cardiac signal is altered by such body impedance, cardiac feature, non-cardiac signal, and/or combination thereof.

Provided herein is a method of simulating an analog electrophysiologic signal comprising providing a digital waveform of a cardiac signal or an analog waveform of the cardiac signal, wherein the cardiac signal comprises an intracardiac electrogram, a surface electrocardiogram, or a test signal from a database of cardiac signals, altering the cardiac signal by combining either the digital waveform or the analog waveform with a simulated body impedance, a non-cardiac signal, or a combination thereof, thereby generating a digital simulated waveform or an analog simulated waveform, converting the digital simulated waveform, if generated, to the analog simulated waveform, providing to a first test system the analog simulated waveform, providing to the evaluator the analog simulated waveform and/or the digital simulated waveform, and information about the digital waveform or an analog waveform of the cardiac signal, and/or whichever simulated body impedance, cardiac feature, and/or non-cardiac signal was used to generate the analog simulated waveform or the digital simulated waveform.

In some embodiments, the non-cardiac signal comprises a noise signal, a baseline wander signal, or an artifact signal. In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the simulator comprises the database. In some embodiments, the first test system comprises at least one of a recorder and a mapping system.

In some embodiments, providing the analog simulated waveform comprises providing a coupling that can be used to couple a simulator that generated the analog simulated waveform to a junction box and providing a coupling that can be used to couple the junction box to the first test system. In some embodiments, the coupling couples the junction box to the first test system couples the junction box to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector.

In some embodiments, the method comprises combining the cardiac signal with the non-cardiac signal. In some embodiments, the method comprises combining the digital waveform of the cardiac signal, the analog waveform of the cardiac signal, the digital simulated waveform or the analog simulated waveform with the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, a default AV disassociation with a subsidiary escape pacemaker that takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), nonspecific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature may be added to the digital waveform or to the analog waveform at a level that is close to the boundary of an abnormality in such a cardiac feature. Depending on the feature, this may be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

In some embodiments, the information comprises how the cardiac signal was altered. In some embodiments, the information comprises the digital waveform or analog waveform of the cardiac signal. In some embodiments, the information comprises the simulated body impedance, and/or the non-cardiac signal used to generate the analog simulated waveform or the digital simulated waveform. In some embodiments, the information comprises the digital waveform or analog waveform of the cardiac signal as combined with the cardiac feature. In some embodiments, the information further comprises the simulated body impedance and/or the non-cardiac signal used to generate the analog simulated waveform or the digital simulated waveform.

In some embodiments, the method comprises providing controls that allow a user to choose or provide the cardiac signal to be altered, choose or provide the simulated body impedance, the non-cardiac signal, and/or the combination thereof that is used to alter the digital waveform or the analog waveform of the cardiac signal, and/or choose the amount by which the cardiac signal is altered by such body impedance, non-cardiac signal, and/or combination thereof.

In some embodiments, the method comprises providing controls that allow a user to choose or provide the cardiac signal to be altered, choose or provide the simulated body impedance, the cardiac feature, the non-cardiac signal, and/or the combination thereof that is used to alter the digital waveform or the analog waveform of the cardiac signal, and/or choose the amount by which the cardiac signal is altered by such body impedance, cardiac feature, non-cardiac signal, and/or combination thereof.

In some embodiments, the method comprises providing circuitry that determines for a user which cardiac signal from the database will be altered, which simulated body impedance, non-cardiac signal, and/or combination thereof will be used to alter the digital waveform or the analog waveform of the cardiac signal, and/or the amount by which the cardiac signal is altered by such body impedance, non-cardiac signal, and/or combination thereof.

In some embodiments, the method comprises providing circuitry that determines for a user which cardiac signal from the database will be altered, which simulated body impedance, cardiac feature, non-cardiac signal, and/or combination thereof will be used to alter the digital waveform or the analog waveform of the cardiac signal, and/or the amount by which the cardiac signal is altered by such body impedance, cardiac feature, non-cardiac signal, and/or combination thereof.

A number of systems for generating cardiac waveforms are described in literature. For example: U.S. Pat. No. 4,204,261 (Ruszala et al.) discloses a complex analog signal generator for generating time varying analog signal waveforms, such as electrocardiogram and blood pressure. U.S. Pat. No. 4,736,322 (Clifford) discloses a device and method for simulating the heartbeat, pressure and respiration waveforms of a human being. U.S. Pat. No. 5,041,973 (Lebron et al.) teaches a cardiac mapping system simulator, while U.S. Pat. No. 7,917,774 (Ruiter) teaches system, methods and apparatuses that produce human physiological waveforms. Each of these references is incorporated by reference in their entirety herein.

Evaluator

A device (digital signal processing and evaluation platform (DSPEP), or signal processing evaluator, or "evaluator") that allows for objectively evaluating the accuracy of a test system, such as an EP recording system's acquisition strategy, is provided herein. It can measure and characterize how the different signal processing schemes used by EP recording systems (to eliminate noise, baseline wander and artifacts) during acquisition affect the true spatiotemporal characteristics of cardiac signals generated by the body.

In some embodiments, a workstation 102 may be located remotely from a DSPEP 100 and/or from a database 108 that comprises a repository of cardiac and/or non-cardiac signals to allow for a centralized database 108; or it may be located locally (FIG. 1A, 1B, or 1C) to allow for an individual at the workstation 102 to tailor, update, manipulate, and/or operate the database 108.

In some embodiments, the test signal database 108 comprises the various cardiac signals 112 and non-cardiac signals 136. The database 108 in such an embodiment may reside with the DSPEP 100 of the workstation 102. The DSPEP is alternatively called an evaluator 100 herein. The test signal database 108 may be constructed by combining data from public sources (for example, MIT's database), previously recorded and annotated EP studies, ECG and IC data scanned from paper recordings and various other sources. This database 108 may also contain a test signal 112 (alternatively called a cardiac signal 112 herein) or multiple test signals 112a, 112b, etc., from cardiac and/or various non-cardiac sources. In some embodiments, non-cardiac sources of cardiac signals may include waveforms specified by various EC standards for testing of medical recorders developed by the American National Standard Institute and the Association for the Advancement of Medical Instrumentation (ANSI/AAMI). The database 108 may also include a non-cardiac test signal 136 (or multiple non-cardiac test signals) that can emulate noise, baseline wander and artifacts similar to real EP recording situations. This database 108 may have an open architecture so that additional or new signals (cardiac signals or non-cardiac signals) can be added.

A computer 118 in the field may be located close to the EP recorder 101 or EP electroanatomical mapping system 104 (either or both of the EP recorder or the EP electroanatomical mapping system may alternatively called a device under test and/or a test system). The computer 118 may have a database connection 110 to the workstation 102 that can download the test signal database 108 from the workstation 102, or can download the cardiac signal 112 and/or a non-cardiac test signal 136. The computer 118 may be connected to the EP cardiac signal simulator 130 using a USB port or other type of interface which is called a simulator connection 116 herein. Galvanic isolation may also be provided between the computer 118 and the EP cardiac simulator 130, so the simulator 130 is electrically isolated from the computer 118.

The database connection 110 may be local or remote.

Figure 1A:
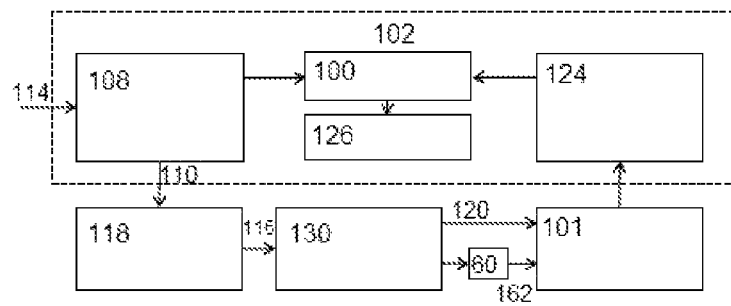
FIG. 1A depicts a block diagram of an embodiment of a system wherein an EP recorder is under test and workstation is remote.

FIG. 1A, therefore, depicts a block diagram of an embodiment of a system wherein an EP recorder is under test and workstation 102 is remote. In this embodiment, test signals (cardiac signals, non-cardiac signals, and/or simulated body impedance) may be put into the database 108 as depicted by arrow 114. The database 108 may store test signals (cardiac signals, non-cardiac signals, and/or simulated body impedance) and a user may choose which test signals are to be used to evaluate the test system using the computer 118, which may receive the test signals chosen by a user from the database 108 through database connection 110. Alternatively, the computer 118 may be set to randomly choose a cardiac signal 112, non-cardiac signal 136, and/or simulated body impedance 132 to combine therewith. The database 108 may be remote from the computer 118, or reside within the computer 118. The database connection 110 may be wired or wireless. Indeed, any connection herein that is not a catheter-based or wire-based connection intended to simulate the effect of a signal passed through such catheter or wire in a patient, may be wired or wireless. In the embodiment of FIG. 1A, the computer 118 combines the cardiac signal with a non-cardiac signal and/or with a simulated body impedance, and delivers this simulated waveform (in digital or analog form) to the simulator 130 through simulator connection 116. In the embodiment of FIG. 1A, the simulator 130 delivers the signal to the EP recorder 101 (the test system in this embodiment) as an analog signal through a test system connection, such as an ECG cable or other cable 120, or through a junction box 60 connected to the simulator and to an electrophysiology catheter connector, which may be a electrophysiology catheter handle (arrow 162). The test system 101 may then filter the signal it receives from the simulator 130 and generate digital output files 124, alternatively called a processed signal, a first processed signal, or a recorded signal herein. The first processed signal 124 may then be received by the digital signal processing and evaluation platform (DSPEP) 100, alternatively called the evaluator herein. In certain embodiments, the evaluator 100 also receives the cardiac signal from the database 108, and may also receive the non-cardiac signal 136 and/or the simulated body impedance 132 that was used to generate the simulated waveform (digital or analog) from the database 108. The evaluator 100 may then generate a first finding 126, which may be in the form of a report or other output that can be seen or used by a user which is based on how well the test system filtered the simulated waveform it received from the simulator. This may be done by comparing the cardiac signal to the first processed signal. This process may be repeated any number of times and with variations chosen in order to generate additional findings regarding how well the test system retains certain cardiac features, or how well it filters the non-cardiac signal and/or the simulated body impedance from the analog simulated waveform it received. The process may be repeated for multiple test systems in order to generate a comparative evaluation of several test systems given controlled and known challenge test signals. For example, if test systems are known to not allow detection of a certain cardiac feature, this cardiac feature may be added to a cardiac signal and multiple test systems may be evaluated in order to determine which test system best allows for detection of this cardiac feature.

Figure 1B:
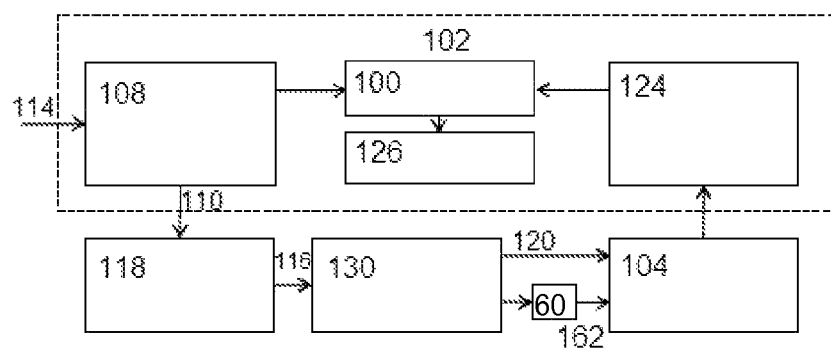
FIG. 1B depicts a block diagram of an embodiment of a simulator wherein the EP mapping system is under test and workstation is remote.

FIG. 1B, therefore, depicts a block diagram of an embodiment of a system wherein an EP mapping system 104 is the device under test and workstation 102 is remote. In this embodiment, test signals (cardiac signals, non-cardiac signals, and/or simulated body impedance) may be put into the database 108 as depicted by arrow 114. The database 108 stores test signals (cardiac signals, non-cardiac signals, and/or simulated body impedance) and a user may choose which test signals are to be used to evaluate the test system using the computer 118, which may receive the test signals chosen by a user from the database 108 through database connection 110. Alternatively, the computer 118 may be set to randomly choose a cardiac signal 112, non-cardiac signal 136, and/or simulated body impedance 132 to combine therewith. The database 108 may be remote from the computer 118, or reside within the computer 118. The database connection 110 may be wired or wireless. Indeed, any connection herein that is not a catheter-based or wire-based connection intended to simulate the effect of a signal passed through such catheter or wire in a patient, may be wired or wireless. In the embodiment of FIG. 1B, the computer 118 combines the cardiac signal with a non-cardiac signal and/or with a simulated body impedance, and delivers this simulated waveform (in digital or analog form) to the simulator 130 through simulator connection 116. In the embodiment of FIG. 1B, the simulator 130 delivers the signal to the EP electroanatomical mapping system 104 (the test system in this embodiment) as an analog signal through a test system connection, such as an ECG cable or other cable 120, or through a junction box 60 connected to the simulator and to an electrophysiology catheter connector, which may be a electrophysiology catheter handle (arrow 162). The test system 104 may then filter the signal it receives from the simulator 130 and generates digital output files 124, alternatively called a processed signal, a first processed signal, or a recorded signal herein. The first processed signal 124 may then be received by the digital signal processing and evaluation platform (DSPEP) 100, alternatively called the evaluator herein. In certain embodiments, the evaluator 100 also receives the cardiac signal from the database 108, and may also receive the non-cardiac signal 136 and/or the simulated body impedance 132 that was used to generate the simulated waveform (digital or analog) from the database 108. The evaluator 100 may then generate a first finding 126, which may be in the form of a report or other output that can be seen or used by a user which is based on how well the test system filtered the simulated waveform it received from the simulator. This may be done by comparing the cardiac signal to the first processed signal. This process may be repeated any number of times and with variations chosen in order to generate additional findings regarding how well the test system retains certain cardiac features, or how well it filters the non-cardiac signal and/or the simulated body impedance from the analog simulated waveform it received. The process may be repeated for multiple test systems in order to generate a comparative evaluation of several test systems given controlled and known challenge test signals. For example, if test systems are known to not allow detection of a certain cardiac feature, this cardiac feature may be added to a cardiac signal and multiple test systems may be evaluated in order to determine which test system best allows for detection of this cardiac feature.

Figure 1C:
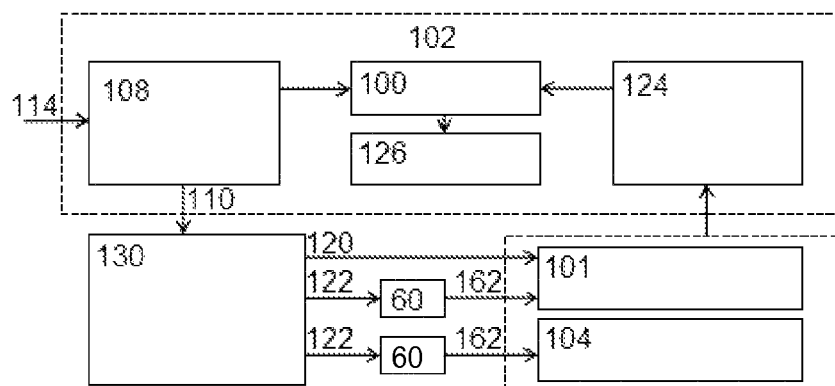
FIG. 1C depicts a block diagram of an embodiment of a system wherein the workstation is local.

FIG. 1C depicts a block diagram of an embodiment of a system wherein an EP recorder 101 and/or an EP electroanatomical mapping system 104 are under test and workstation 102 is remote from the simulator and/or the test systems (EP recorder 101 and/or the EP mapping system 104, for example). In this embodiment, test signals (cardiac signals, non-cardiac signals, and/or simulated body impedance) may be put into the database 108 as depicted by arrow 114. The database 108 may store test signals (cardiac signals, non-cardiac signals, and/or simulated body impedance) which may be further transmitted to an EP cardiac signal simulator 130 via database connection 110. The simulator 130 may deliver a signal to an EP recorder 101 through a test system connection, such as an ECG cable or other cable 120 and/or through a junction box 60 connected to the simulator (arrow 122) and to an electrophysiology catheter connector, which may be an electrophysiology catheter handle (arrow 162). Alternatively or additionally, the simulator 130 may deliver analog signals to an EP electroanatomical mapping system 104 directly using a cable, catheter, or other connection, or through a junction box 60. The test systems 101 and/or 104 may then filter the signal it receives from the simulator 130 and generate digital output files 124, alternatively called a processed signal, a first processed signal, or a recorded signal herein. The first processed signal 124 is then received by the digital signal processing and evaluation platform (DSPEP) 100, alternatively called the evaluator herein. In certain embodiments, the evaluator 100 may receive the cardiac signal 112 from the database 108, and may also receive a non-cardiac signal 136 and/or the simulated body impedance 132 that was used to generate the simulated waveform (digital or analog) from the database 108. The evaluator 100 may then generate a first finding 126, which may be in the form of a report or other output that can be seen or used by a user which is based on how well the test system filtered the simulated waveform it received from the simulator. This may be done by comparing the cardiac signal to the first processed signal. This process may be repeated any number of times and with variations chosen in order to generate additional findings regarding how well the test system retains certain cardiac features, or how well the test system filters the non-cardiac signal and/or the simulated body impedance from the analog simulated waveform it received. The process may be repeated for multiple test systems in order to generate a comparative evaluation of several test systems given controlled and known challenge test signals. For example, if test systems are known to not allow detection of a certain cardiac feature, this cardiac feature may be added to a cardiac signal and multiple test systems may be evaluated in order to determine which test system best allows for detection of this cardiac feature.

In FIGS. 1A, 1B, and 1C, the workstation 102 is depicted as comprising the database 108, the evaluator 100, and the first processed signal 124 (or digital files generated by the test system), and comprising the first finding 126. However, in certain embodiments, the workstation 102 comprises one or more of the database 108, the evaluator 100, and the first processed signal 124 (or digital files generated by the test system), and comprising the first finding 126. In certain embodiments, the workstation 102 comprises a computer 118. In certain embodiments, the workstation 102 comprises the simulator 130. In certain embodiments, the workstation comprises a junction box 60 that connects to an EP recorder or a junction box 60 that connects to an EP Mapping System, or elements thereof.

Figure 2:
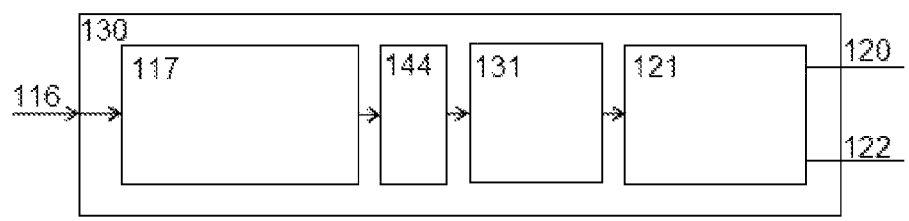
FIG. 2 depicts a block diagram of an embodiment of the EP simulator.

The EP simulator 130 (as depicted in FIG. 2 as an example embodiment) contains a microcontroller 117 which receives the various cardiac signals 112 and non-cardiac signals 136 from the database 108 of the workstation 102. In some embodiments, the database 108 resides on the computer 118 as part of the workstation 102. In other embodiments, the database 108 resides on a computer 118 separate from the workstation and the workstation pulls the various cardiac signals 112 and non-cardiac signals 136 from the database 108. In some embodiments, the EP simulator 130 may contain a microcontroller 117 which receives the various cardiac signals 112 and non-cardiac signals 136 from the database 108 or the computer 118 which may be a part of workstation 102. In yet other embodiments, a computer 118 is separate from the workstation and receives the various cardiac signals 112 and non-cardiac signals 136 from the database 108 which is part of the workstation 102. The microcontroller 117 controls the digital to analog (D/A) converter 144. When instructed by the microcontroller 117, the D/A converter 144 may generate analog waveshapes 113 (alternatively called analog waveforms of the cardiac signal herein), based on the digital data of the cardiac signal, which may or may not include a non-cardiac signal added thereto from the database 108. After signal conditioning (e.g. conversion by the D/A converter 144), simulated body impedance may be added to the analog waveform of the cardiac signal (which may or may not include a non-cardiac signal added thereto). In such embodiment, the D/A converter is connected to various resistors, capacitors and inductive networks which simulate different body impedances 132 and alter the waveform of the cardiac signal (which may or may not include a non-cardiac signal added thereto) to generate the analog simulated waveform. Different body impedances 132 may be used to simulate different signal conditioning coming from the electrode-body connections encountered in real EP recordings. The output of EP simulator 130 may mimic the human body and provide simulated analog cardiac signals 142.

The EP simulator 130 may also provide ECG and intracardiac connectors 121 that allow the EP recording system 102 to connect to the EP simulator 130 with its own cables. The same cable 120 that is used during EP studies to connect the EP recorder 101 or the EP electroanatomical mapping system 104 to the patient in order to record surface electrocardiograms (ECG) may be used. This cable 120 may provide connections to the ECG electrodes (typically, but not restricted to: four limb leads; left arm (LA), left leg (LL), right arm (RA) and right leg (RL), and six precordial leads V1, V2, V3, V4, V5 and V6). The EP simulator 130 also may also provide special connectors for intracardiac signals. These connectors may allow connections to the EP recorder 101 via the junction box 60.

FIG. 2, therefore, depicts an embodiment of an EP simulator 130 receiving various input signals through a USB port or other type of interface 116, wherein the EP simulator 130 contains a microcontroller 117 that controls the D/A converter 144. In the depicted embodiment, a body impedance simulator 131 may modify resultant analog signals from a D/A converter 144 which are delivered as output or signals using ECG and/or and IC connections 121 via an ECG cable or other cable 120 to a test system such as an EP recorder, EP mapping system, evaluator and or other device, or via a connection (arrow 122) to a junction box which connects to a test system such as an EP recorder, EP mapping system, evaluator and or other device.

Figure 3:
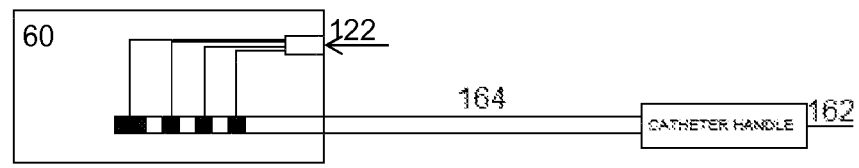
FIG. 3 depicts a block diagram of an example of an embodiment of an EP catheter.

In some embodiments, the same connectors on the EP simulator 130 may allow connection to the EP electroanatomical mapping system 104, such as is depicted in FIG. 3. In that case the junction box 60 may provide places for one or more EP catheters 164 and has connections for the cable (arrow 122) to enable connection with EP simulator 130. The handle of the catheter 162 may be connected in various EP settings to an RF generator, patient interface unit or directly to an EP electroanatomical mapping system 104.

FIG. 3, therefore, depicts a block diagram of an embodiment of a junction box 60, wherein a cable for the junction box connects (at arrow 122) the junction box to the simulator, and a catheter and electrophysiology catheter connector 162 may deliver signals from an EP simulator 130 through the junction box to a test system such as an EP recorder 101 or EP electroanatomical mapping system 104 or another test system.

In some embodiments, the EP recorder 101 or EP electroanatomical mapping system 104 is set up to acquire cardiac signals 112 and non-cardiac signals 136 from the simulator 130 as they would be if connected to a real patient during EP studies. Analog and digital filters used to remove noise and artifacts may be used in the same fashion as they would be used during EP studies. Digital output recordings 124 may be stored in the same fashion as they would be during EP studies.

In some embodiments, digital data recorded by the EP recorder 101 or EP electroanatomical mapping system 104 are transferred manually or electronically to the workstation 102 and stored as digital output files 124.

In some embodiments, the digital database 108 and digital output 124 may be compared using DSPEP 100. The effect of various digital signal processing schemes and filters used for removing noise, baseline wander and artifacts may be compared, viewed and completely evaluated off-line. A first finding 126 may be generated to include various test results.

In some embodiments, different signal processing tools and signal comparison modules in the workstation 102 allow for analysis of cardiac signal waveform time and frequency. These tools may be used to evaluate differences between the original signal from database 108 and the recorded signal 124 acquired by EP recorder 101 or EP electroanatomical mapping system 104. DSPEP 100 may allow for different software modules to be added, enhancing signal processing and analysis.

In some embodiments, digital signal processing tools in the workstation 102 allow for adding, removing or mixing together various components of the database 108 which comprise cardiac signals 112 and non-cardiac signals 136, to simulate and mimic various recording situations encountered in a real EP environment.

Provided herein is a signal processing evaluator comprising: a digital waveform of a cardiac signal or an analog waveform of the cardiac signal, a first processed signal received from a first test system, wherein the first processed signal is the result of digital processing of an analog simulated waveform by the first test system, wherein the analog simulated waveform was generated by combining the digital waveform of the cardiac signal or the analog waveform of the cardiac signal with a simulated body impedance, a non-cardiac signal, and/or a combination thereof, and third circuitry that compares the digital waveform of the cardiac signal or the analog waveform of the cardiac signal to the first processed signal and generates a first finding evaluating the first test system.

In some embodiments, the first finding depicts or describes how closely matched the first processed signal is to the digital waveform of the cardiac signal or to the analog waveform of the cardiac signal.

In some embodiments, the evaluator comprises information about the simulated body impedance, the non-cardiac signal, and/or the combination thereof that was used to generate the analog simulated waveform.

In some embodiments, the second circuitry compares the first finding to a second finding, evaluating a second test system. In some embodiments, the second finding depicts or describes how closely matched a second processed signal that is the result of digital processing of the analog simulated waveform by a second test system is to the digital waveform of the cardiac signal or to the analog waveform, and generates an evaluation regarding which of the first test system and the second test system better processes the analog simulated waveform.

In some embodiments, the first finding expresses the effectiveness of the first test system in reproducing the digital waveform of the cardiac signal or the analog waveform of the cardiac signal from the analog simulated waveform.

In some embodiments, the first circuitry is configured to compare a second digital waveform of a second cardiac signal or second analog waveform of the second cardiac signal to a second processed signal. In some embodiments, the second processed signal is a result of digital processing of a second analog simulated waveform by the first test system, wherein the second analog simulated waveform is generated based on the second digital waveform of the second cardiac signal or the second analog waveform of the cardiac signal and a second simulated body impedance, a second non-cardiac signal, and/or a combination thereof.

In some embodiments, the digital waveform of the cardiac signal or the analog waveform of the cardiac signal comprises a cardiac feature. In some embodiments, the first finding expresses how well the first test system preserves the cardiac feature in the first processed signal as compared to the digital waveform of the cardiac signal or to the analog waveform of the cardiac signal.

In some embodiments, the evaluator comprises information about the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker that takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), non-specific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature may be added to the digital waveform or to the analog waveform at a level that is close to the boundary of an abnormality in such cardiac feature. Depending on the feature, this may be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

In some embodiments, the first finding expresses how well the first test system removes the non-cardiac signal from the analog simulated waveform. In some embodiments, the first finding expresses how well the first test system removes the simulated body impedance from the analog simulated waveform. In some embodiments, the first circuitry is configured to assess the first processed signal and the digital waveform of the cardiac signal or the analog waveform of the cardiac signal in the time domain, frequency domain, or a combination thereof.

In some embodiments, the non-cardiac signal comprises a noise signal, a baseline wander signal, or an artifact signal. In some embodiments, cardiac signal comprises an intracardiac electrogram, a surface electrocardiogram, or a test signal. In some embodiments, the test signal comprises an Electrocardiograph Committee (EC) standard waveform. In some embodiments, the EC standard waveform is a standard for testing the recorder or the mapping system as defined by ANSI or AAMI. In some embodiments, the cardiac signal comprises one or more of an electrocardiogram, a unipolar electrogram, and a bipolar electrogram. In some embodiments, the first processed signal comprises a reconstructed cardiac activation map or data necessary to generate the reconstructed cardiac activation map.

In some embodiments, the first test system comprises at least one of a recorder and a mapping system. In some embodiments, the recorder comprises an electrophysiology recorder. In some embodiments, the mapping system comprises an electrophysiology mapping system. In some embodiments, the first test system comprises an analog filter or a digital filter or a combination thereof configured to process the analog simulated waveform in order to generate the first processed signal.

In some embodiments, the evaluator comprises an evaluator connection to the first test system. In some embodiments, the evaluator comprises a database or a database connection to a database, wherein the database comprises the cardiac signal, and at least one of the simulated body impedance and the non-cardiac signal. In some embodiments, the database comprises a cardiac feature.

In some embodiments, the evaluator comprises first circuitry configured to alter the cardiac signal by combining the digital waveform of the cardiac signal or the analog waveform of the cardiac signal with the simulated body impedance, the non-cardiac signal, or a combination thereof, thereby generating a digital simulated waveform or an analog simulated waveform. In some embodiments, the evaluator comprises a D/A converter configured to convert the digital simulated waveform to the analog simulated waveform. In some embodiments, the evaluator comprises the database.

In some embodiments, the first test system comprises at least one of a recorder and a mapping system. In some embodiments, the test system connection couples to a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector. In some embodiments, the simulator comprises the junction box.

Provided herein is a method comprising: providing a signal processing evaluator to a user, wherein the evaluator comprises a digital waveform of a cardiac signal or an analog waveform of the cardiac signal, a first processed signal received from a first test system, wherein the first processed signal is the result of digital processing of an analog simulated waveform by the first test system, wherein the analog simulated waveform was generated by combining the digital waveform of the cardiac signal or the analog waveform of the cardiac signal with a simulated body impedance, a non-cardiac signal, and/or a combination thereof, and third circuitry that compares the digital waveform of the cardiac signal or the analog waveform of the cardiac signal to the first processed signal and generates a first finding evaluating the first test system.

Provided herein is a method comprising: receiving a first processed signal from a first test system, wherein the first processed signal is the result of digital processing of an analog simulated waveform by the first test system, wherein the analog simulated waveform was generated by combining a digital waveform of a cardiac signal or an analog waveform of the cardiac signal with a simulated body impedance, a non-cardiac signal, and/or a combination thereof, comparing the digital waveform of the cardiac signal or the analog waveform of the cardiac signal to the first processed signal, generating a first finding that evaluates the first test system, and providing the first finding to a user.

In some embodiments, the first finding depicts or describes how closely matched the first processed signal is to the digital waveform of the cardiac signal or to the analog waveform of the cardiac signal.

In some embodiments, the method comprises providing information about the simulated body impedance, the non-cardiac signal, and/or the combination thereof that was used to generate the analog simulated waveform. In some embodiments, the method comprises comparing the first finding to a second finding evaluating a second test system.

In some embodiments, the second finding depicts or describes how closely matched a second processed signal that is the result of digital processing of the analog simulated waveform by a second test system is to the digital waveform of the cardiac signal or to the analog waveform, and generates an evaluation regarding which of the first test system and the second test system better processes the analog simulated waveform.

In some embodiments, the first finding expresses the effectiveness of the first test system in reproducing the digital waveform of the cardiac signal or the analog waveform of the cardiac signal from the analog simulated waveform.

In some embodiments, the method comprises comparing a second digital waveform of a second cardiac signal or second analog waveform of the second cardiac signal to a second processed signal. In some embodiments, the second processed signal is a result of digital processing of a second analog simulated waveform by the first test system, wherein the second analog simulated waveform is generated based on the second digital waveform of the second cardiac signal or the second analog waveform of the cardiac signal and a second simulated body impedance, a second non-cardiac signal, and/or a combination thereof.

In some embodiments, the digital waveform of the cardiac signal or the analog waveform of the cardiac signal comprises a cardiac feature. In some embodiments, the first finding expresses how well the first test system preserves the cardiac feature in the first processed signal as compared to the digital waveform of the cardiac signal or to the analog waveform of the cardiac signal.

In some embodiments, the method comprises providing information about the cardiac feature.

In some embodiments, the cardiac feature comprises a parameter having a parameter value, a change in the parameter value, a shape of one or more parameters, or a change that alters the shape of the analog simulated waveform or a portion thereof.

In some embodiments, the cardiac feature comprises a parameter of an electrocardiogram waveform or of an electrogram waveform. In some embodiments, the parameter comprises: an RR interval, a P wave, a PR interval, a PR segment, a QRS complex, a J-point, an ST segment, a T wave, an ST interval, a QT interval, a U wave, a J wave, or a combination thereof.

In some embodiments, the cardiac feature comprises a change in the cardiac signal that is indicative of a disease.

In some embodiments, the disease is myocardial infarction. In some embodiments, myocardial infarction may be exhibited by a change in the cardiac signal over time that includes ST elevation, Q wave formation, T wave inversion, and normalization with a persistent Q wave. Thus, in certain embodiments, the cardiac feature comprises a change in the cardiac signal over time that includes ST elevation, Q wave formation, T wave inversion, and normalization with a persistent Q wave.

In some embodiments, the disease is pulmonary embolism. In some embodiments, pulmonary embolism may be shown by one or more of S-waves in Lead I of a surface electrode 12-lead ECG, and Q-waves and inverted T-waves in Lead III of the surface electrode 12-lead ECG. Thus, in certain embodiments, the cardiac feature comprises S-waves in Lead I of a surface electrode 12-lead ECG, and Q-waves and inverted T-waves in Lead III of the surface electrode 12-lead ECG.

In some embodiments, the cardiac feature comprises a rhythm abnormality. In some embodiments, the cardiac feature comprises a conduction abnormality. In some embodiments, the cardiac feature comprises a change in the cardiac signal indicative of a sinus arrhythmia such as sinus tachycardia (>90 beats per minute); sinus bradycardia (<50 beats per minute); sinus arrhythmia; sinus arrest or pause; and/or sino-atrial exit block. In some embodiments, the cardiac feature comprises a change in the cardiac signal indicative of a sinus valve (SV) arrhythmia such as a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, and/or paroxysmal supraventricular tachycardia.

In some embodiments, the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, and/or atrial flutter with 2:1 block. In some embodiments, the junctional tachycardia comprises: exit block, no exit block, AV block, and/or no AV block.

In some embodiments, the cardiac feature comprises a change in the cardiac signal indicative of a ventricular arrhythmia such as a premature ventricular complex, a ventricular escape or rhythm, an accelerated ventricular rhythm, uniform ventricular tachycardia, polymorphous ventricular tachycardia, torsade ventricular tachycardia, and/or ventricular fibrillation.

In some embodiments, the cardiac feature comprises a change in the cardiac signal indicative of an atrioventricular conduction abnormality such as a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, and/or a usurpation AV disassociation with incomplete AV dissociation due to accelerated ventricular rhythm.

In some embodiments, the cardiac feature comprises a change in the cardiac signal indicative of intraventricular conduction abnormality such as complete LBBB (fixed or intermittent), incomplete LBBB, left anterior fascicular block (LAFB), left posterior fascicular block (LPFB), non-specific intraventricular conduction defect (IVCD), and/or a Wolff-Parkinson-White (WPW) pre-excitation pattern.

In some embodiments, the cardiac feature comprises a change in the cardiac signal related to the QRS pattern and/or the voltage of the cardiac signal such as complete LBBB (fixed or intermittent), incomplete LBBB, left anterior fascicular block (LAFB), left posterior fascicular block (LPFB), low voltage frontal plane (QRS amplitude <0.5 mV), and/or low voltage precordial leads (QRS amplitude <1.0 mV).

In some embodiments, the cardiac feature comprises a change in the cardiac signal indicative of hypertrophy or enlargement of a cardiac anatomic aspect such as left atrial enlargement, right atrial enlargement, left ventricular hypertrophy, and/or right ventricular hypertrophy.

In some embodiments, the cardiac feature comprises a change in the cardiac signal reflecting a ST-T and/or U abnormality such as left atrial enlargement, nonspecific ST-T abnormalities such as a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, and/or prolonged QT interval.

In some embodiments, the cardiac feature comprises a change in the cardiac signal reflecting myocardial infarctions (MIs) including acute, recent, and old MIs, such as inferior MI, inferoposterior MI, inferoposterolateral MI, true posterior MI, anteroseptal MI, anterior MI, anterolateral MI, high lateral MI, non Q-wave MI, and/or right ventricular MI.

In some embodiments, the cardiac feature comprises a change in the cardiac signal reflecting clinical disorders such as chronic pulmonary disease, hypokalemia such as giant TU fusion waves, hyperkalemia, hypocalcemia, hypercalcemia, and/or digoxin effects.

In some embodiments, the cardiac feature comprises a change in the cardiac signal listed in the Minnesota ECG Code Classification System.

In some embodiments, a level, power, and/or amount of the cardiac feature is at about the abnormality boundary for the cardiac feature. That is, the cardiac feature is added to the digital waveform or to the analog waveform at a level that is close to the boundary of an abnormality in such cardiac feature. Depending on the feature, this may be expressed in any number of ways, as a voltage level, a time, a duration, a pattern, a slope, and any identifiable feature on the given waveform in time domain, frequency domain or any other form of the waveform (whether digital or analog). Such abnormalities may be indicative of an onset of an abnormality or of an almost abnormal cardiac feature, according to various coding guides, such as the Minnesota ECG Code Classification System, or another Code or classification system for non-limiting example.

In some embodiments, a level, power, and/or amount of the cardiac feature is at about a limit of detection for the test system under evaluation, for example the first test system or the second test system, at least. In some embodiments, a level, power, and/or amount of the cardiac feature, the simulated body impedance, and/or the non-cardiac signal is at about a detectability boundary of the first test system or of a second test system. In some embodiments, the detectability boundary is </=20 times the minimum detectability limit of the first test system. In some embodiments, the detectability boundary is </=10 times the minimum detectability limit of the first test system. In some embodiments, the detectability boundary is </=5 times the minimum detectability limit of the first test system. In some embodiments, the detectability boundary is </=3 times the minimum detectability limit of the first test system. In some embodiments, the detectability boundary is </=2 times the minimum detectability limit of the first test system. The term "about" as used herein with regard to the detectability limit refers to variability of +/−10%, +/−25%, or +/−50%, depending on the embodiment.

In some embodiments, the first finding expresses how well the first test system removes the non-cardiac signal from the analog simulated waveform. In some embodiments, the first finding expresses how well the first test system removes the simulated body impedance from the analog simulated waveform.

In some embodiments, the method comprises assessing the first processed signal and the digital waveform of the cardiac signal or the analog waveform of the cardiac signal in the time domain, frequency domain, or a combination thereof.

In some embodiments, the non-cardiac signal comprises a noise signal, a baseline wander signal, or an artifact signal. In some embodiments, the cardiac signal comprises an intracardiac electrogram, a surface electrocardiogram, or a test signal. In some embodiments, the test signal comprises an Electrocardiograph Committee (EC) standard waveform. In some embodiments, the EC standard waveform is a standard for testing the recorder or the mapping system as defined by ANSI or AAMI.

In some embodiments, the first test system comprises at least one of a recorder and a mapping system. In some embodiments, the recorder comprises an electrophysiology recorder. In some embodiments, the mapping system comprises an electrophysiology mapping system. In some embodiments, the first test system comprises an analog filter or a digital filter or a combination thereof configured to process the analog simulated waveform in order to generate the first processed signal. In some embodiments, the cardiac signal comprises one or more of an electrocardiogram, a unipolar electrogram, and a bipolar electrogram. In some embodiments, the first processed signal comprises a reconstructed cardiac activation map or data necessary to generate the reconstructed cardiac activation map.

In some embodiments, the method comprises generating the analog simulated waveform by combining the digital waveform of the cardiac signal or the analog waveform of the cardiac signal with the simulated body impedance, the non-cardiac signal, or the combination thereof. In some embodiments, the method comprises converting a digital simulated waveform of the digital waveform of the cardiac signal as combined with the simulated body impedance, the non-cardiac signal, or the combination thereof to the analog simulated waveform. In some embodiments, the method comprises receiving one or more of the digital waveforms of the cardiac signal, the analog waveform of the cardiac signal, the simulated body impedance, the non-cardiac signal, or a cardiac feature from a database.

In some embodiments, the first test system comprises at least one of a recorder and a mapping system.

In some embodiments, the method comprises providing a junction box which couples to the first test system. In some embodiments, the junction box couples to an amplifier of the first test system. In some embodiments, the junction box comprises at least one electrophysiology catheter connector. In some embodiments, the junction box comprises multiple electrophysiology catheter connectors. In some embodiments, each of the electrophysiology catheter connectors couples a different brand or version of electrophysiology catheter to the first test system. In some embodiments, the junction box comprises a universal electrophysiology catheter connector that can couple multiple brands or versions of electrophysiology catheters to the first test system using the universal electrophysiology catheter connector.

As used herein ordinals such as first, second, third, etc. are used merely for clarity in drafting, and not intended to imply first in time, importance, or any other aspect, unless otherwise identified and described with regard to the element.

Example 3

FIG. 16 depicts the method of evaluating how well a test system filters simulated body impedance and non-cardiac signals from an analog simulated signal, and preserves certain cardiac features or modifications to a cardiac signal. Step 216 retrieves the digital simulated waveform from a simulator, such as the digital simulated waveform generated in Step 204 of FIG. 14, or generated in Step 212 of FIG. 15. Step 218 retrieves the processed signal from the test system. As discussed herein, the processed signal is the result of digital processing of the analog simulated waveform (such as that generated in Step 206 of either FIG. 14 or FIG. 15, for example), by the first test system, wherein the analog simulated waveform was generated by combining the digital waveform of the cardiac signal or the analog waveform of the cardiac signal with a simulated body impedance, a non-cardiac signal, a cardiac feature and/or a combination thereof. Step 220 of FIG. 16 compares the digital simulated waveform to the processed signal. This comparison may be by simple subtraction of these signals, or by another comparison means, in order to generate an objective finding of how well the test system filters the simulated body impedance or the non-cardiac signal without losing the basic features of the cardiac signal or of a cardiac feature within such signal or that was combined with such signal, as shown in Step 222 of FIG. 16.

Example 4

Figure 17:
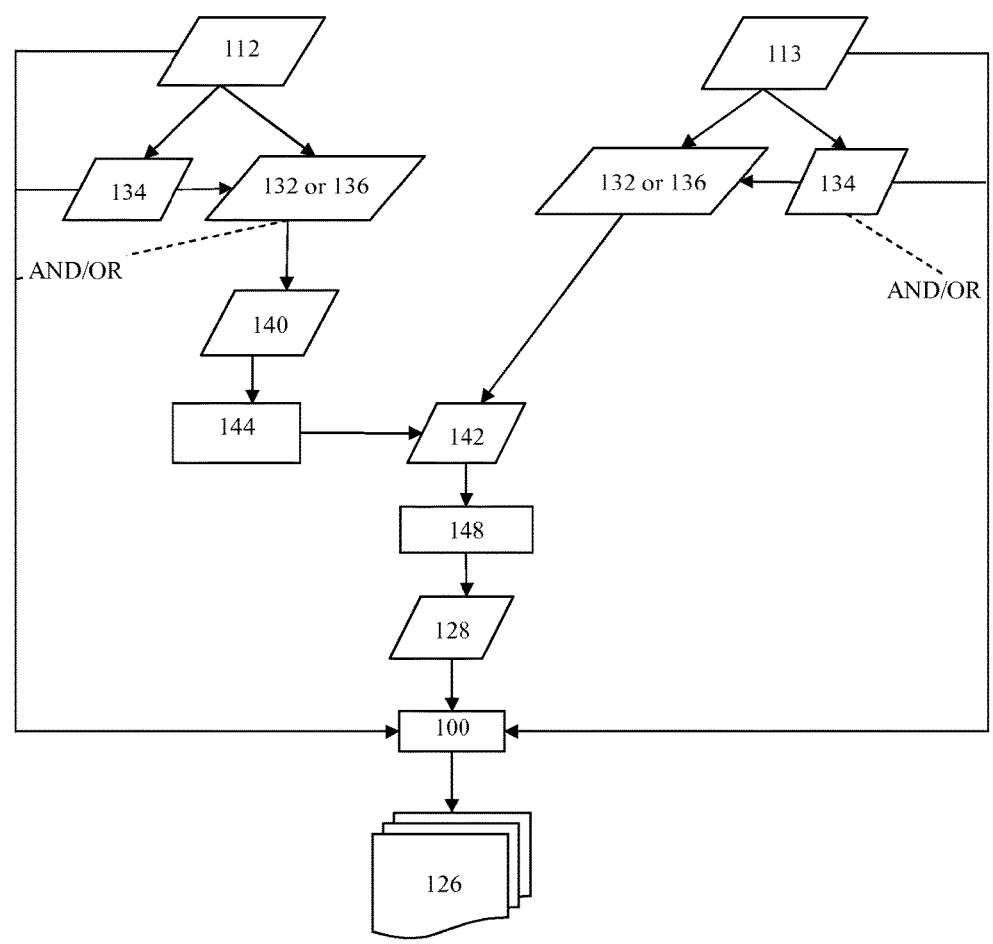
FIG. 17 depicts the embodiment of a flow of data from the database into the EP simulator and into the evaluator which compares the original data and the data after testing under the EP recorder, EP mapping system, or both.

FIG. 17 depicts the embodiment of a flow of data from the database into the EP simulator and into the evaluator which compares the original data and the data after testing under the EP recorder, EP mapping system, or both. In this figure, starting on the left side from the top, a cardiac signal 112 is provided from a database 108 (not shown) and a non-cardiac signal 136, a cardiac feature 134, a simulated impedance 132, or a combination thereof may be added to the cardiac signal 112 in order to form a digital simulated waveform 140. The digital simulated waveform may be converted by a D/A converter 144 into an analog simulated waveform 142, which is then transferred to a first test system 148 which generates a first processed signal 128 in either analog or digital form. As an alternative embodiment (not shown), the simulated impedance 132 may be added after the conversion of the digital simulated waveform 140 into the analog simulated waveform 142. Thus, the digital simulated waveform 140 prior to conversion may comprise a combination of a cardiac signal 112 and a cardiac feature 134 or a combination of a cardiac signal 112 and a non-cardiac signal 136, or may comprise only the cardiac signal 112. Once converted into analog form, the simulated impedance 132 may be added or generated and added in order to generate the analog simulated waveform 142.

In another embodiment, starting on the right side from the top of FIG. 17, an cardiac signal in analog form 113 may be provided and a non-cardiac signal 136, a cardiac feature 134, a simulated impedance 132, or a combination thereof may be added to the cardiac signal 113 in order to form an analog simulated waveform 140. In order to make this change to the cardiac signal, it may be necessary to convert the analog form of the cardiac signal 113 to a digital form using a A/D converter, then alter the digital form of the cardiac signal, and then convert this back to an analog form. The simulated impedance 132 may be added or generated and added to the cardiac signal at any stage prior to delivery to the test system. That is, it may be added before or after D/A conversion, or not added at all. The analog simulated waveform 142, may then be transferred to a first test system 148 which generates a first processed signal 128 in either analog or digital form.

The first processed signal 128 may be then transferred to the evaluator 100, which also receives at least the digital form of the cardiac signal 112 or the analog form of the cardiac signal 113. The evaluator 100 may also receive the cardiac feature 134, the simulated impedance 132, the non-cardiac signal 136, or some combination thereof that was used to generate the analog simulated waveform. Alternatively, the evaluator may receive some information about the cardiac feature 134, the simulated impedance 132, the non-cardiac signal 136, which may not be the actual waveform itself, but rather information which indicates how the cardiac signal was altered (for non-limiting example: cardiac feature change type or extent, disease simulation, electrocardiogram waveform parameter change, abnormality type). The evaluator 100 may then take the first processed signal 128 and compare it to the cardiac signal 112 or a digital form of the analog cardiac signal 113 that was sent to the test system to determine how well the test system filters the simulated impedance and/or the non-cardiac features from the analog simulated waveform, and generate a first finding 126 indicating how well this filtering was done. The first finding 126 may also or alternatively indicate how well a cardiac feature was preserved by the test system, or whether such cardiac feature was detected or detectable in the first processed signal. The cardiac feature may have been one added to the cardiac signal, or may have been existing in the cardiac signal received from the database. Multiple findings may be generated using different challenges of variables sent to the test system or to multiple test systems.

A user will be able to choose the cardiac signal, whether or not to add a cardiac feature or to choose a cardiac signal already exhibiting a particular cardiac feature, whether or not to add a non-cardiac signal to the cardiac signal, and whether or not to add simulated impedance to the cardiac signal. This choice may be done at a workstation that is either remote to or local to the simulator that delivers the analog simulated waveform reflecting these user choices to the first test system. Alternatively, a computer program may randomly or methodically challenge the test system using any one or more of these variables (cardiac signal, cardiac features, non-cardiac signals, simulated impedance) as described infra. Multiple test systems may be fed the same or different analog simulated waveforms to evaluate these test systems alone or in comparison with each other. The evaluator may also be remote to or local to the simulator that delivers the analog simulated waveform reflecting these user choices to the first test system. In some embodiments a computer comprises logic, hardware, software, and/or circuitry that allows a user to choose the inputs to the test system (cardiac signal, cardiac feature, simulated impedance, non-cardiac feature) and comprises the evaluator and its logic, hardware, software, and/or circuitry configured to compare the inputs to the first processed signal, at least, and generates the output first finding 126, or a plurality of findings.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An electrophysiology (EP) simulator for determining the accuracy of an EP recorder or mapping system in the acquisition of cardiac signals comprising
    (a) a database connection to a database, wherein the database is configured to store:
        i. a cardiac signal expressed in a digital waveform or an analog waveform, and
        ii. a simulated body impedance waveform, a cardiac feature waveform, or a non-cardiac signal waveform;
    (b) a first circuitry that alters the cardiac signal by combining:
        i. the cardiac signal and;
        ii. the simulated body impedance waveform, the non-cardiac signal waveform, the cardiac feature waveform, or a combination thereof, thereby generating a digital simulated waveform or an analog simulated waveform;
    (c) a D/A converter that converts the digital simulated waveform to the analog simulated waveform;
    (d) a first connection to a first test system, wherein the first test system is an EP recorder system or a mapping system;
    (e) a second connection to a first evaluator, wherein the second connection couples the EP simulator to an evaluator; and
    (f) a second circuitry that provides to the first evaluator:
        i. the cardiac signal; and
        ii. information about whichever the simulated body impedance waveform, the cardiac feature waveform, or the non-cardiac signal waveform used to generate the analog simulated waveform or the digital simulated waveform.

2. The simulator of claim 1, wherein the cardiac signal comprises one or more of the following: an electrocardiogram, a unipolar electrogram, a bipolar electrogram, a cardiac activation map, and a data necessary to generate the cardiac activation map.

3. The simulator of claim 1, wherein the cardiac feature waveform comprises a parameter comprising a parameter value, a change parameter, a shape value parameter, a shape change parameter that alters the shape of the analog simulated waveform or a portion thereof value, or any combination thereof.

4. The simulator of claim 1, wherein the cardiac feature comprises a parameter of an electrocardiogram waveform or of an electrogram waveform, the parameter comprising an RR interval, a P wave, a PR interval, a PR segment, a QRS complex, a J-point, an ST segment, a T wave, an ST interval, a QT interval, a U wave, a J wave, or a combination thereof.

5. The simulator of claim 3, wherein the cardiac feature waveform comprises a change parameter value in the cardiac signal over time that includes a ST elevation, a Q wave formation, a T wave inversion, and a Q-wave normalization with a persistent Q wave parameter.

6. The simulator of claim 1, wherein the cardiac feature waveform comprises S-waves in Lead I of a surface electrode 12-lead ECG, and Q-waves, and inverted T-waves in Lead III of the surface electrode 12-lead ECG.

7. The simulator of claim 1, wherein the cardiac feature waveform comprises a change in the cardiac signal associated with indicative of a sinus arrhythmia, sinus bradycardia, sinus arrhythmia, sinus arrest or pause, sino-atrial exit block, a sinus valve (SV) arrhythmia, a non-conducted premature atrial complex (PAC), a normally conducted PAC, a PAC conducted with aberration, ectopic atrial rhythm or tachycardia (unifocal), multifocal atrial rhythm or tachycardia, atrial fibrillation, atrial flutter, premature junctional complex, junctional escapes or rhythms, accelerated junctional rhythms, junctional tachycardia, or paroxysmal supraventricular tachycardia.

8. The simulator of claim 7, wherein the atrial flutter comprises: atrial flutter with 2:1 atrioventricular (AV) conduction, atrial flutter with 3:2 conduction ratio, atrial flutter with variable AV block and rate-dependent left bundle branch block (LBBB), LBBB and atrial flutter with 2:1 AV block, atrial flutter with 2:1 and 4:1 conduction and rate dependent LBBB, atrial flutter with variable AV block, atrial flutter with 2:1 conduction, or atrial flutter with 2:1 block.

9. The simulator of claim 1, wherein the cardiac feature waveform comprises a change in the cardiac signal associated with indicative of a ventricular arrhythmia, a premature ventricular complex, a ventricular escape or rhythm, an accelerated ventricular rhythm, uniform ventricular tachycardia, polymorphous ventricular tachycardia, torsade ventricular tachycardia, or ventricular fibrillation.

10. The simulator of claim 1, wherein the cardiac feature waveform comprises a change in the cardiac signal associated with indicative of an atrioventricular conduction abnormality comprising a first degree AV block, a first degree AV block with a left atrial abnormality, a type I second degree AV block (Wenckebach), a type II second degree AV block (Mobitz), an advanced or high grade AV block, a third degree AV block, a third degree AV block with junctional escape rhythm, a third degree AV block with ventricular escape rhythm, a default AV disassociation, and a default AV disassociation with a subsidiary escape pacemaker takes over by default, a usurpation AV disassociation, or a usurpation AV disassociation with incomplete AV dissociation due to accelerated ventricular rhythm.

11. The simulator of claim 1, wherein the cardiac feature waveform comprises a change in the cardiac signal associated with indicative of intraventricular conduction abnormality, complete LBBB (fixed or intermittent), incomplete LBBB, left anterior fascicular block (LAFB), left posterior fascicular block (LPFB), nonspecific intraventricular conduction defect (IVCD), or a Wolff-Parkinson-White (WPW) pre-excitation pattern.

12. The simulator of claim 1, wherein the cardiac feature waveform comprises a pattern change in the cardiac signal, the cardiac signal comprising a cardiac signal related to waveform associated with a the QRS pattern, complete LBBB (fixed or intermittent), incomplete LBBB, left anterior fascicular block (LAFB), left posterior fascicular block (LPFB), low voltage frontal plane (QRS amplitude <0.5 mV), or low voltage precordial leads (QRS amplitude <1.0 mV).

13. The simulator of claim 1, wherein the cardiac feature waveform comprises a change in the cardiac signal associated with indicative of hypertrophy or enlargement of a cardiac anatomic aspect, left atrial enlargement, right atrial enlargement, left ventricular hypertrophy, or right ventricular hypertrophy.

14. The simulator of claim 1, wherein the cardiac feature waveform comprises a change in the cardiac signal associated with reflecting a ST-T and/or U abnormality, left atrial enlargement, nonspecific ST-T abnormalities, a ST segment depression, ST elevation (transmural injury), ST elevation (pericarditis pattern), symmetrical T wave inversion, symmetrical T wave inversion reflecting inferior myocardial infarction (MI) (fully evolved), hyperacute T waves, prominent upright U waves, U wave inversion, or prolonged QT interval.

15. The simulator of claim 1, wherein the cardiac feature waveform comprises a change in the cardiac signal associated with reflecting myocardial infarctions (MIs) including acute, recent, and old MIs, inferior MI, inferoposterior MI, inferoposterolateral MI, true posterior MI, anteroseptal MI, anterior MI, anterolateral MI, high lateral MI, non Q-wave MI, or right ventricular MI.

16. The simulator of claim 1, wherein the cardiac feature waveform comprises a change in the cardiac signal associated with reflecting clinical disorders, the clinical disorders comprising chronic pulmonary disease, hypokalemia, giant TU fusion waves, hyperkalemia, hypocalcemia, hypercalcemia, or digoxin effects.

17. The simulator of claim 1, wherein: (a) the first circuitry alters the cardiac signal by combining a set abnormality boundary level, power, and/or amount of cardiac feature waveform with the simulated body impedance waveform, the non-cardiac signal waveform, or a combination thereof is at about the abnormality boundary for the cardiac feature waveform; (b) a level, power, and/or amount of the cardiac feature waveform, the simulated body impedance, and/or the non-cardiac signal waveform is at about a detectability boundary of the first test system or of a second test system; and (c) the detectability boundary is "N" times the minimum detectability limit of the first test system, the value of N being selected by one of the following: equal to or less than 2, equal to or less than 3, equal to or less than 5, equal to or less than 10, and equal to or less than 20.

18. The simulator of claim 17, wherein the set abnormality boundary level is about 1 to 20 times a detectability boundary of the EP recorder.

* * * * *